(12) United States Patent
Richard et al.

(10) Patent No.: US 11,458,083 B2
(45) Date of Patent: *Oct. 4, 2022

(54) COSMETIC AND/OR DERMATOLOGICAL COMPOSITION CONTAINING A MEROCYANINE DERIVATIVE COMPRISING SPECIFIC POLAR GROUPS CONSISTING OF HYDROXYL- AND ETHER-FUNCTIONALITIES

(75) Inventors: Herve Richard, Gagny (FR); Xavier Marat, Paris (FR); Florence L'Alloret, Paris (FR); Didier Candau, Bievres (FR); Julie Songeur-Geney, Saint Cloud (FR); Julie Grumelard, Huningue (FR); Barbara Winkler, Lörrach (DE); Dietmar Huglin, Reihen (CH)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/233,603

(22) PCT Filed: Jul. 19, 2012

(86) PCT No.: PCT/EP2012/064195
§ 371 (c)(1),
(2), (4) Date: Apr. 18, 2014

(87) PCT Pub. No.: WO2013/011094
PCT Pub. Date: Jan. 24, 2013

(65) Prior Publication Data
US 2014/0294743 A1 Oct. 2, 2014

(30) Foreign Application Priority Data
Jul. 21, 2011 (WO) ................ PCT/EP2011/062522

(51) Int. Cl.
| | | |
|---|---|---|
| *A61K 8/44* | (2006.01) | |
| *A61K 8/42* | (2006.01) | |
| *A61K 8/49* | (2006.01) | |
| *A61Q 17/04* | (2006.01) | |
| *A61K 8/41* | (2006.01) | |
| *A61K 8/34* | (2006.01) | |

(52) U.S. Cl.
CPC ............. *A61K 8/44* (2013.01); *A61K 8/347* (2013.01); *A61K 8/41* (2013.01); *A61K 8/42* (2013.01); *A61K 8/49* (2013.01); *A61K 8/4926* (2013.01); *A61K 8/4973* (2013.01); *A61Q 17/04* (2013.01)

(58) Field of Classification Search
CPC ... A61K 8/41; A61K 8/42; A61K 8/49; A61K 8/4926; A61K 8/4973; A61K 8/347; A61K 8/44; A61Q 17/04
See application file for complete search history.

(56) References Cited

U.S. PATENT DOCUMENTS

| | | | |
|---|---|---|---|
| 4,749,643 A | 6/1988 | Ohlschläger et al. | |
| 5,624,663 A | 4/1997 | Deflandre et al. | |
| 8,961,941 B2* | 2/2015 | Richard | A61K 8/35 |
| | | | 424/401 |
| 9,550,730 B2* | 1/2017 | Winkler | C07D 317/28 |
| 9,993,405 B2* | 6/2018 | Roudot | A61K 8/41 |
| 2009/0264657 A1* | 10/2009 | Wagner | A61K 8/347 |
| | | | 546/242 |
| 2013/0064871 A1* | 3/2013 | Richard | A61K 8/35 |
| | | | 424/401 |

(Continued)

FOREIGN PATENT DOCUMENTS

| | | |
|---|---|---|
| DE | 3505423 A1 | 8/1986 |
| FR | 2957251 A1 | 9/2011 |

(Continued)

*Primary Examiner* — Blessing M Fubara
(74) *Attorney, Agent, or Firm* — Polsinelli PC

(57) ABSTRACT

The present invention relates to a cosmetic and/or dermatological composition comprising in a physiologically acceptable medium at least one merocyanine derivative of formula (1) or (2) and/or its E,E-, E,Z- or Z,Z-geometrical isomer forms: comprising specific polar groups consisting of hydroxyl- and ether-functionalities. Another object of the present invention relates to a cosmetic process for controlling and/or improving the darkening of the skin under exposure to UV radiation and the homogeneity of the colour of the complexion which comprises the application onto the skin of a cosmetic composition as above defined. Another object of the present invention relates to a cosmetic process for protecting the keratinic materials and particularly the skin against photo-ageing which comprises the application onto the keratinic material of a cosmetic composition as above defined.

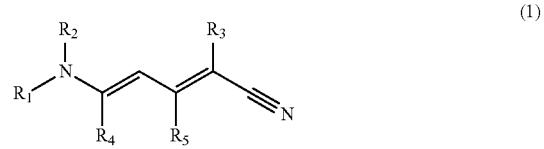

(1)

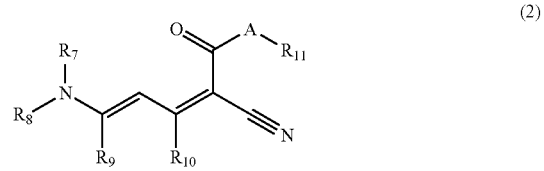

(2)

26 Claims, No Drawings

(56) References Cited

U.S. PATENT DOCUMENTS

| | | | | |
|---|---|---|---|---|
| 2013/0251650 A1* | 9/2013 | Winkler | ............... | A61K 8/40 424/59 |
| 2015/0133015 A1* | 5/2015 | Cano Carrasquilla | .. | B32B 27/12 442/71 |
| 2015/0284330 A1* | 10/2015 | Richard | ............... | A61K 8/35 546/246 |

FOREIGN PATENT DOCUMENTS

| | | | |
|---|---|---|---|
| GB | 2 416 351 A | * | 1/2006 |
| GB | 2 416 351 A | | 1/2006 |
| GB | 2445635 A | | 7/2008 |
| JP | 2005-538072 A | | 12/2005 |
| JP | 2010-516725 A | | 5/2010 |
| JP | 2010-536822 A | | 12/2010 |
| JP | 2011-506558 A | | 3/2011 |
| JP | 4703606 B2 | | 3/2011 |
| JP | 2011-073214 A | | 4/2011 |
| RU | 2 144 350 C1 | | 1/2000 |
| RU | 2 203 033 C2 | | 4/2003 |
| WO | WO-2004/006878 A1 | | 1/2004 |
| WO | WO-2007/014848 A2 | | 2/2007 |
| WO | WO-2007/017848 A2 | | 2/2007 |
| WO | WO-2008/090066 A2 | | 7/2008 |
| WO | WO-2009/027258 A2 | | 3/2009 |
| WO | WO-2009/080661 | | 7/2009 |
| WO | WO-2010/083368 A2 | | 7/2010 |
| WO | WO-2010/097480 A2 | | 9/2010 |
| WO | WO 2011/113718 A1 | * | 9/2011 |
| WO | WO-2011/113718 A1 | | 9/2011 |
| WO | WO-2011/113719 A2 | | 9/2011 |
| WO | WO-2013/010590 A1 | | 1/2013 |
| WO | WO-2013/011480 A1 | | 1/2013 |

\* cited by examiner

COSMETIC AND/OR DERMATOLOGICAL COMPOSITION CONTAINING A MEROCYANINE DERIVATIVE COMPRISING SPECIFIC POLAR GROUPS CONSISTING OF HYDROXYL- AND ETHER-FUNCTIONALITIES

CROSS REFERENCE TO RELATED APPLICATIONS

This application is a National Phase filing under 35 U.S.C. § 371 of PCT/EP2011/064195 filed on Jul. 19, 2012; which in turn claims priority to Application No. PCT/EP2011/062522 filed on Jul. 21, 2011; the entire contents of all are hereby incorporated by reference.

THE NAMES OF THE PARTIES TO A JOINT RESEARCH AGREEMENT

The inventions disclosed and claimed herein were made pursuant to a Joint Development Agreement that was in effect on or before the time the claimed inventions were made, between L'ORÉAL and BASF SE.

The present invention relates to new cosmetic and/or dermatological compositions for a topical use, in particular intended for controlling the darkening of the skin and/or preventing the photo-aging of keratinic materials in particular the skin under exposure of UV radiations comprising in a physiologically acceptable medium at least one merocyanine derivative comprising specific polar groups consisting of hydroxyl- and ether-functionalities of formula (1) or (2) which will be detailed below.

It relates also to cosmetic and/or dermatological compositions comprising in a physiologically acceptable medium at least one merocyanine of formula (1) or (2) and further a system for screening out both UVA radiation and UVB radiation It is known that light radiation with wavelengths between 280 nm and 400 nm permits tanning of the human epidermis and that rays with wavelengths between 280 and 320 nm, which are known as UV-B rays, harm the development of a natural tan. This exposure is also susceptible to also induce an alteration of the biomechanical properties of epidermis which is expressed by the appearance of wrinkles leading to a premature ageing of the skin.

It is also known that UV-A rays, with wavelengths between 320 and 400 nm, penetrate more deeply into the skin than the UV-B rays. UV-A rays promote an immediate and persistent darkening of the skin. A daily exposure to the UVA radiation, even in a short time, in normal conditions, can generate a degradation of the collagen fibers and elastin which is expressed by a modification of the skin micro-relief, the appearance of wrinkles and an irregular pigmentation (ie brown spots, unhomogeneity of the complexion . . . ).

A protection against UVA and UVB radiations is therefore necessary. An efficient photoprotective product must protect both UVA and UVB radiations.

Many photoprotective cosmetic compositions for the skin have been proposed to date. They contain generally organic UV filters and inorganic UV filters which work according to their own chemical nature and according to their own physical properties by absorption, reflexion or diffusion of the UV radiations. They generally contain combinations of organic oil-soluble UV filters and/or organic water-soluble UV filters associated to metal oxide pigments as titanium dioxide ($TiO_2$).

Many cosmetic compositions intended for limiting the darkening of the skin, improving the colour and the homogeneity of the complexion have been proposed to date. In order to obtain such compositions, it is well-known for a skilled man in the field of suncare products to use UV filters in particular UVB filters. Certain compositions may further contain UVA filters. This filtering system has to cover the UVB protection in order to limit and control the neo-synthesis of melanin promoting the global pigmentation but also has to cover the UVA protection in order to limit and control the oxidation of already present melanins leading to a darkening of the skin color.

But no composition contains a particular combination of UV filters which is specifically adapted to the photoprotection of the skin and particularly to an improvement of the quality of the skin both at the level of the colour and of its elasticity mechanical properties.

In an advantageous way, this improvement is particularly visible on already pigmented skins in order not to increase the pigmentary load in melanin neither the structure of the melanin which is already present into the skin.

In fact, most of the organic UV screening agents are aromatic compounds absorbing in the zone between 280 nm and 370 nm. Besides their filtering power of the solar radiation, the desired photoprotecting compounds must also present good cosmetic properties, a good solubility in usual solvents and in particular in fatty substances as oils, greases and also a good photostability alone and in association with other UV filters. They must be also colorless or at least present a cosmetically acceptable colour for the consumer.

One of the major drawbacks of those compositions known until this day is that those filtering systems are insufficiently photoprotective against UV radiations and particularly against long UVA radiations with wavelengths beyond 370 nm in order to control the photo-induced pigmentation and its evolution by an appropriate UV filtering system covering the whole UV spectrum.

Amongst all the compounds which were recommended for this effect, we can mention the particularly interesting UV filters family which consists in carbonated merocyanine derivatives which is disclosed in the U.S. Pat. No. 4,195,999 or the application WO2004/006878. Those compounds present very good filtering properties in the long UVA rays but have a little satisfactory solubility in usual solvents and in particular in fatty substances as the oils and a not satisfactory photostability for certain families of merocyanines Therefore, there is still a need for finding new merocyanine compounds active in the long UVA which present good cosmetic properties, a good solubility in cosmetic oily or aqueous solvents, a good compatibility with other complementary UVA filters as the dibenzoylmethane derivatives, specifically regarding photostability and also a cosmetically acceptable colour for the consumer.

However, after considerable research conducted in the field of photoprotection mentioned above, the Applicant has now discovered, surprisingly, that this objective could be reached with a new family of merocyanine derivatives comprising specific polar groups consisting of hydroxyl- and ether-functionalities and corresponding to the formula (1) or (2) which will be detailed below.

This discovery forms the basis of the present invention.

A first object of the present invention relates to a cosmetic and/or dermatological composition comprising in a physiologically acceptable medium at least one merocyanine derivative of formula (1) or (2) which will be detailed below.

Another object of the present invention related to a cosmetic and/or dermatological composition comprising in a physiologically acceptable medium at least one merocyanine of formula (1) or (2) and further a system for screening out both UVA radiation and UVB radiation Another object of the present invention related to a cosmetic and/or dermatological composition comprising in a physiologically acceptable medium at least one merocyanine derivative of formula (1) or (2) and at least one dibenzoylmethane derivative.

A third object of the present invention relates to a cosmetic process for controlling and/or improving the darkening of the skin under exposure to UV radiation and the homogeneity of the colour of the complexion which comprises the application onto the skin of a cosmetic composition as above defined.

Another object of the present invention relates to a cosmetic process for protecting the keratinic materials and particularly the skin against photo-ageing which comprises the application onto the keratinic material of a cosmetic composition as above defined.

Other characteristics, aspects and advantages of the present invention will emerge on reading the detailed description that follows.

The term "physiologically acceptable" means compatible with the skin and/or its integuments, which has a pleasant colour, odour and feel and which does not cause any unacceptable discomfort (stinging, tautness or redness) liable to put the consumer off using this composition.

The term "keratinic materials" includes the skin, the scalp, the hair, eyelashes, eyebrows and nails.

In the rest of the present description, the expression "system for screening out both UVA radiation and UVB radiation" is intended to mean an agent for screening out UVA radiation with wavelengths between 320 and 400 nm and UVB radiation with wavelengths between 280 and 320 nm, constituted of either a mixture of several organic compounds and/or inorganic compounds for screening out said UV radiation, for example a mixture comprising a UVA screening agent and a UVB screening agent, or else an organic compound for screening out both UVA radiation and UVB radiation.

According to the present invention the merocyanine derivatives correspond to the following formula (1) or (2)

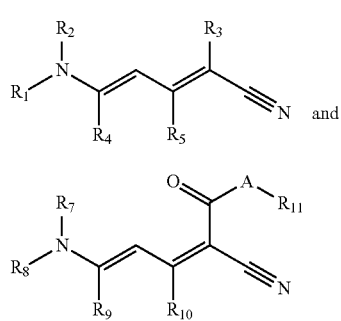

$R_1$ and $R_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or R1 and R2 together with the nitrogen atom linking them form a —(CH$_2$)$_n$— ring which is optionally interrupted by —O— or by —NH—;

$R_3$ is a —(C═O)OR6group; or a —(CO)NHR$_6$group;
$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which is optionally substituted by $C_1$-$C_4$alkyl and/or interrupted by one or more than one —O— or by —NH—;
n is a number from 2 to 7;
$R_7$ and $R_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH, $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;
or $R_7$ and $R_8$ together with the nitrogen atom linking them form a —(CH$_2$)$_n$— ring which is optionally interrupted by one or more than one —O—;
$R_9$ and $R_{10}$ are hydrogen; or R9 and R10 form a —(CH$_2$)$_n$— ring which is optionally substituted by C1-C4alkyl and/or interrupted by —O— or by —NH—;
A is —O—; or —NH;
$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one 0; or $C_1$-$C_{22}$alkyl or $C_2$-$C_{22}$alkenyl which is substituted by $C_3$-$C_{22}$cycloalkyl or $C_3$-$C_{22}$cycloalkenyl, wherein said $C_3$-$C_{22}$cycloalkyl or $C_3$-$C_{22}$cycloalkenyl is optionally interrupted by one or more than one —O—;
with the proviso that
(I) at least one of $R_1$, $R_2$ and $R_6$ is substituted by hydroxy;
(II) if one of $R_1$ is hydroxyethyl, $R_2$ is not hydrogen, methyl or ethyl or hydroxyethyl; and if $R_1$ is hydrogen, R2 is not 1-hydroxy-3-methyl-but-2-yl;
(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical;
(IV) at least one of $R_7$ and $R_8$, or $R_{11}$ is interrupted by one or more than one —O—.

Preferred are compounds of formula (1) or (2), wherein $R_1$ and $R_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or $R_1$ and $R_2$ together with the nitrogen atom linking them form a —(CH$_2$)$_n$— ring which is optionally interrupted by —O— or by —NH—;
R3 is a —(C═O)OR$_6$group; or a —(CO)NHR$_6$group;
R6 is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which is optionally substituted by $C_1$-$C_4$alkyl and/or interrupted by —O— or by —NH—;
n is a number from 2 to 7;
$R_7$ and $R_8$ independently of each other are hydrogen; $C_1$-$C_{22}$alkyl, $C_2$-$C_{22}$alkenyl, $C_2$-$C_{22}$alkinyl, which is optionally interrupted by one or more than one 0 and/or substituted by one or more than one OH; or R7 and R8 together with the nitrogen atom linking them form a —(CH2)n- ring which is optionally interrupted by one or more than one —O—;
$R_9$ and $R_{10}$ are hydrogen; or $R_9$ and $R_{10}$ form a —(CH$_2$)$_n$— ring which is optionally substituted by $C_1$-$C_4$alkyl and/or interrupted by —O— or by —NH—;
A is —O—; or —NH;
$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O;

with the proviso that (I) at least one of $R_1$, $R_2$ and $R_6$ is substituted by hydroxy;
(II) if one of $R_1$ is hydroxyethyl, $R_2$ is not hydrogen, methyl or ethyl or hydroxyethyl; and if $R_1$ is hydrogen, R2 is not 1-hydroxy-3-methyl-but-2-yl;
(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical;
(IV) at least one of $R_7$ and $R_8$, or $R_{11}$ is interrupted by one or more than one —O—.

Preferred are compounds of formula (1) or (2), wherein $R_1$ and $R_2$ independently of each other are hydrogen; $C_4$-$C_{12}$alkyl; or hydroxy-$C_3$-$C_{12}$alkyl;
wherein at least one of $R_1$ and $R_2$ is hydroxy-$C_3$-$C_{12}$alkyl; and
$R_3$, $R_4$ and $R_5$ are defined as in claim 1.

Preferred are also compounds of formula (1), wherein $R_6$ is $C_8$-$C_{82}$alkyl, which is optionally substituted by one or more than one hydroxy.

More preferred are also compounds of formula (1), wherein
$R_6$ is $C_1$-$C_{82}$alkyl which is substituted by one or more than one hydroxy;
one of $R_8$ and $R_2$ is $C_4$-$C_{22}$alkyl; or $R_8$ and $R_2$ together with the nitrogen atom linking them form a —(CH$_2$)n-ring which is optionally interrupted by —O— and/or —NH—; and $R_4$ and $R_5$ and n are defined as in claim 1.

Preferred are compounds of formula (2), wherein
$R_{11}$ is a radical of —(CH$_2$)$_m$—O—$R_{12}$, wherein
$R_{12}$ is $C_1$-$C_{12}$alkyl; or $C_1$-$C_6$alkoxy-$C_1$-$C_6$alkyl; m is a number from 1 to 5; and
$R_7$, $R_8$, $R_9$, $R_{10}$ and A are defined as in claim 1.

Even more preferred are compounds of formula (1) or (2) wherein
$R_1$ and $R_2$ and $R_7$ and $R_8$ respectively together with the linking nitrogen atom form a piperidyl radical or a morpholinyl radical.

Preferred are also compounds of formulas (1) and (2), wherein $R_4$ and $R_5$ and $R_9$ and $R_{10}$ respectively form a carbocyclic ring which contains 6 carbon atoms.

Most preferred are compounds of formula (1), wherein $R_1$ and $R_2$ independently of each other are hydrogen; or $C_1$-$C_{22}$alkyl; or hydroxy-$C_1$-$C_{22}$alkyl; or $R_1$ and $R_2$ together with the nitrogen atom are linked together to form a piperidyl or morpholinyl radical;
$R_3$ is a —(C=O)OR$_6$group; or a —(CO)NHR$_6$group;
$R_6$ is $C_1$-$C_{22}$alkyl, which may be substituted by one or more than one —OH;
$R_4$ and $R_5$ are hydrogen; or $R_4$ and $R_5$ are linked together to form a carbocyclic ring which contains 6 carbon atoms.

Most preferred are compounds of formula (1), wherein $R_1$ and $R_2$ independently of each other are hydrogen; or hydroxy-$C_1$-$C_{22}$alkl; wherein at least one of $R_1$ and $R_2$ is hydroxy-$C_1$-$C_{22}$alkyl;
$R_3$ is a —(C=O)OR$_6$ group; or a —(C=O)NHR$_6$ group; $R_6$ is $C_1$-$C_{22}$alkyl; and
$R_4$ and $R_5$ are hydrogen; or $R_4$ and $R_5$ are linked together to form a carbocyclic ring which contains 6 carbon atoms.

Most preferred are compounds of formula (2), wherein $R_7$ and $R_8$ independently of each other are hydrogen or $C_1$-$C_8$alkyl, which is optionally interrupted by one or more than one —O—;

A is —O—; or —NH;
$R_{11}$ is $C_1$-$C_{22}$alkyl; and
$R_9$ and $R_{10}$ are hydrogen; or $R_9$ and $R_{10}$ are linked together to form a carbocyclic ring which contains 6 carbon atoms.

Most preferred are compounds of formula (2), wherein $R_7$ and $R_8$ together with the nitrogen atom form a morpholinyl or piperidyl radical;
A is —O—; or —NH;
$R_{11}$ is $C_1$-$C_{22}$alkyl; which is interrupted by one or more than one —O—; and
$R_9$ and $R_{10}$ are hydrogen; or $R_9$ and $R_{10}$ are linked together to form a carbocyclic ring which contains 6 carbon atoms.

Even more preferred are compounds of formula (2), wherein
$R_{11}$ is a radical of —(CH$_2$)$_m$—O—$R_{12}$, wherein
$R_{12}$ is $C_1$-$C_4$alkyl; or $C_1$-$C_4$alkoxy-C1-$C_4$alkyl;
m is a number from 1 to 3;
$R_7$ and $R_8$, independently of each other are hydrogen; $C_1$-$C_{12}$alkyl, which is optionally interrupted by one or more than one O; or $R_7$ and $R_8$ together with the nitrogen atom form a morpholinyl or piperidyl radical;
$R_9$ and $R_{10}$ are hydrogen; or form a carbocyclic ring which contains 6 carbon atoms; and
A is —O—; or —NH.

The merocyanine compounds of the invention may be in the E/E-, E/Z- or Z/Z geometrical isomer forms.

Alkyl, cycloalkyl, alkenyl, alkylidene or cycloalkenyl may be straight chained or branched, monocyclic or polycyclic.

$C_1$-$C_{22}$alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Substituted alkyl is for example methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)-propyl, ethoxycarbonylmethyl-2-(2-hydroxyethoxy)ethyl or 2-furylethyl.

Hydroxysubstituted alkyl is for example hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

$C_2$-$C_{22}$alkenyl is for example straight-chain $C_2$-$C_{12}$alkenyl or preferably branched $C_3$-$C_{12}$alkenyl. $C_1$-$C_{12}$alkyl, like vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the different isomers of hexenyl, octenyl, nonenyl, decenyl or dodecenyl.

$C_3$-$C_{12}$cycloalkyl is for example cyclopropyl, cyclobutyl, cyclopentyl, trimethylcyclohexyl or preferably cyclohexyl.

Examples of merocyanines according to the present invention are listed in Table A:

TABLE A

| Compound | Structure |
|---|---|
| 1 | (structure: ethyl 2-cyano-5-[bis(2-methoxyethyl)amino]penta-2,4-dienoate) |
| 2 | (structure: 2-methoxyethyl 2-cyano-5-[bis(2-methoxyethyl)amino]penta-2,4-dienoate) |
| 3 | (structure: 2-ethoxyethyl 2-cyano-5-[bis(2-methoxyethyl)amino]penta-2,4-dienoate) |
| 4 | (structure: 2-ethoxyethyl 2-cyano-5-(piperidin-1-yl)penta-2,4-dienoate) |
| 5 | (structure: 2-(2-methoxyethoxy)ethyl 2-cyano-5-(piperidin-1-yl)penta-2,4-dienoate) |
| 6 | (structure: 2-cyano-N-(2-hydroxyethyl)-5-(piperidin-1-yl)penta-2,4-dienamide) |
| 7 | (structure: 2,3-dihydroxypropyl 2-cyano-5-(piperidin-1-yl)penta-2,4-dienoate) |

TABLE A-continued

| Compound | Structure |
| --- | --- |
| 8 | 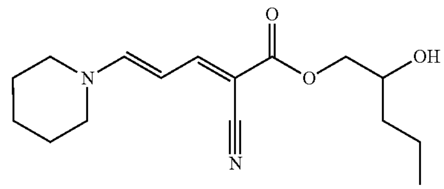 [SMILES: CCCC(O)COC(=O)/C(C#N)=C/C=C/N1CCCCC1] |
| 9 | 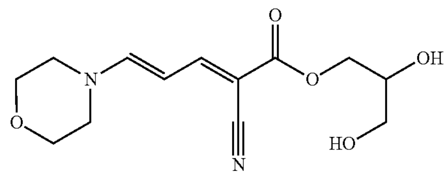 [SMILES: N#C/C(=C\C=C\N1CCOCC1)C(=O)OCC(O)CO] |
| 10 | 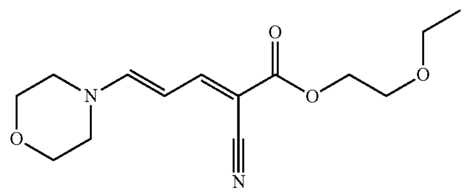 [SMILES: CCOCCOC(=O)/C(C#N)=C/C=C/N1CCOCC1] |
| 11 | 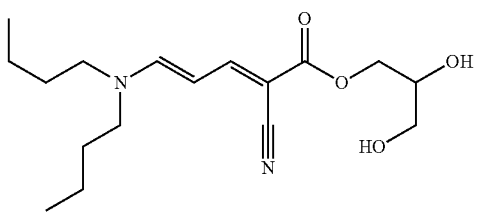 [SMILES: CCCCN(/C=C/C=C(\C#N)C(=O)OCC(O)CO)CCCC] |
| 12 | 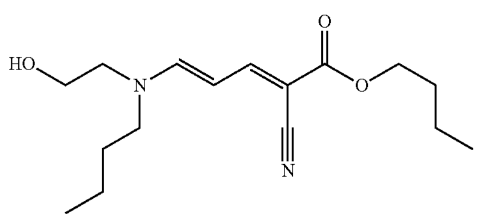 [SMILES: CCCCOC(=O)/C(C#N)=C/C=C/N(CCO)CCCC] |
| 13 | 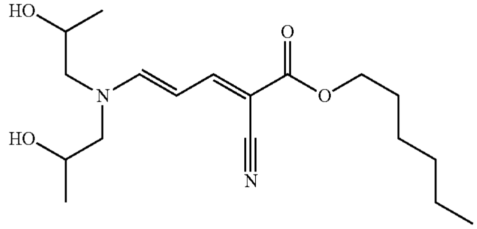 [SMILES: CCCCCCOC(=O)/C(C#N)=C/C=C/N(CC(C)O)CC(C)O] |
| 14 | 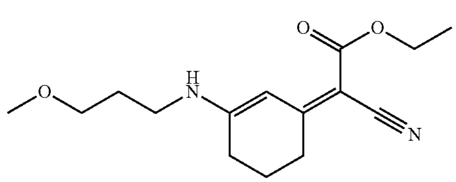 [SMILES: CCOC(=O)/C(C#N)=C1\C=C(NCCCOC)CCC1] |

TABLE A-continued

| Compound | Structure |
|---|---|
| 15 | 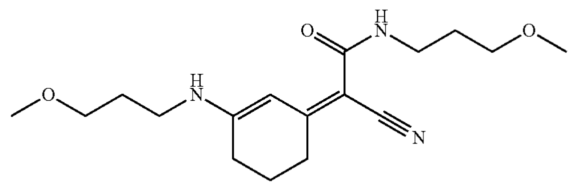 |
| 16 | 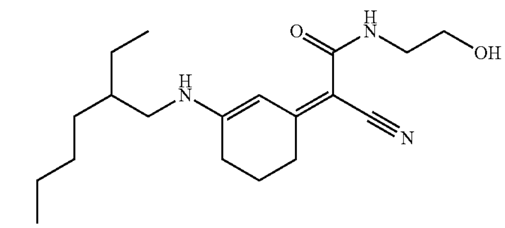 [SMILES: CCCCC(CC)CNC1=C/C(=C(/C#N)C(=O)NCCO)CCC1] |
| 17 | 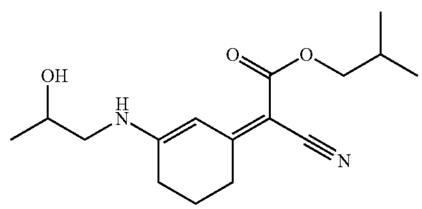 [SMILES: CC(C)COC(=O)/C(C#N)=C1\C=C(NCC(C)O)CCC1] |
| 18 | 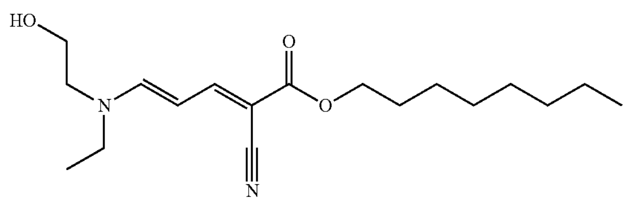 [SMILES: CCCCCCCCOC(=O)/C(C#N)=C/C=C/N(CC)CCO] |
| 19 | 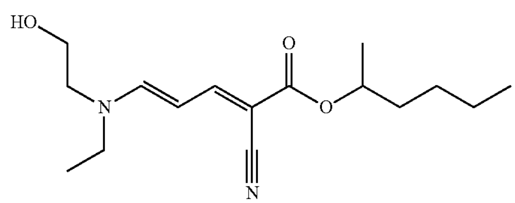 [SMILES: CCCCC(C)OC(=O)/C(C#N)=C/C=C/N(CC)CCO] |
| 20 | 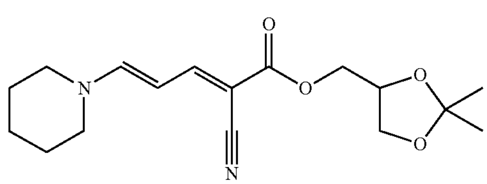 [SMILES: CC1(C)OCC(COC(=O)/C(C#N)=C/C=C/N2CCCCC2)O1] |
| 21 | 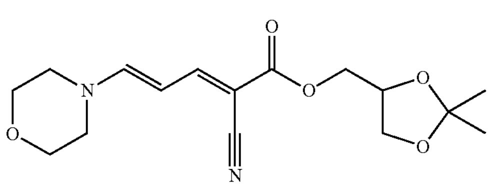 [SMILES: CC1(C)OCC(COC(=O)/C(C#N)=C/C=C/N2CCOCC2)O1] |
| 22 | 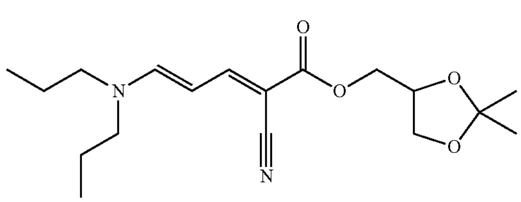 [SMILES: CCCN(/C=C/C=C(\C#N)C(=O)OCC1COC(C)(C)O1)CCC] |

TABLE A-continued

| Compound | Structure |
|---|---|
| 23 | 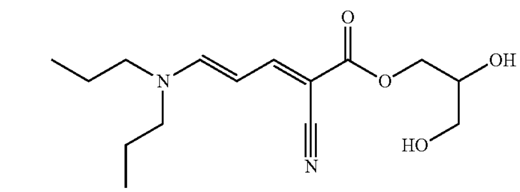 [SMILES: CCCN(/C=C/C=C(\C#N)C(=O)OCC(O)CO)CCC] |
| 24 | 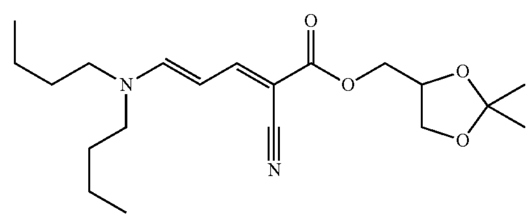 [SMILES: CCCCN(/C=C/C=C(\C#N)C(=O)OCC1COC(C)(C)O1)CCCC] |
| 25 | 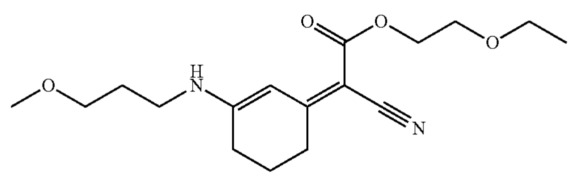 [SMILES: CCOCCOC(=O)/C(C#N)=C1\C=C(NCCCOC)CCC1] |
| 26 | 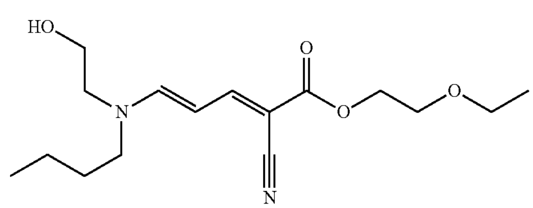 [SMILES: CCCCN(/C=C/C=C(\C#N)C(=O)OCCOCC)CCO] |
| 27 | 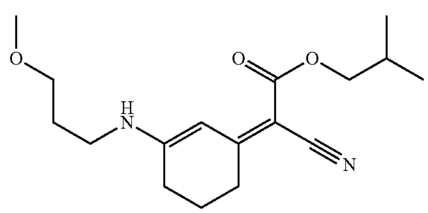 [SMILES: COCCCNC1=C/C(=C(/C#N)C(=O)OCC(C)C)CCC1] |
| 28 | 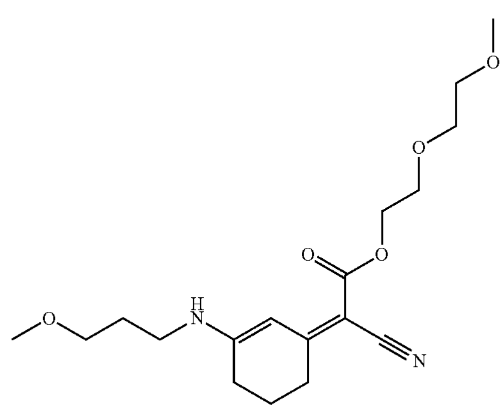 |

TABLE A-continued
| Compound | Structure |
|---|---|
| 29 | 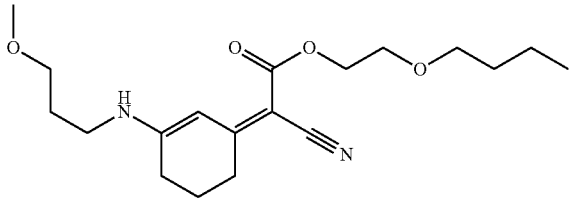 [SMILES: CCCCOCCOC(=O)/C(C#N)=C1\C=C(NCCCOC)CCC1] |
| 30 | 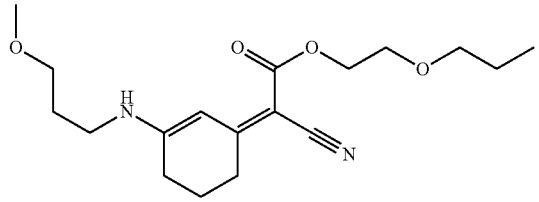 [SMILES: CCCOCCOC(=O)/C(C#N)=C1\C=C(NCCCOC)CCC1] |
| 31 | 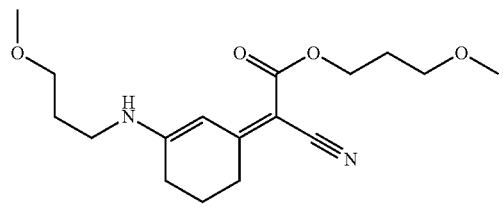 [SMILES: COCCCNC1=C/C(=C(/C#N)C(=O)OCCCOC)CCC1] |
| 32 | 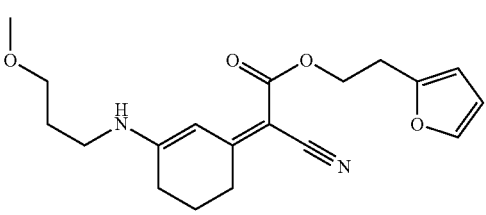 [SMILES: COCCCNC1=C/C(=C(/C#N)C(=O)OCCc2ccco2)CCC1] |
| 33 | 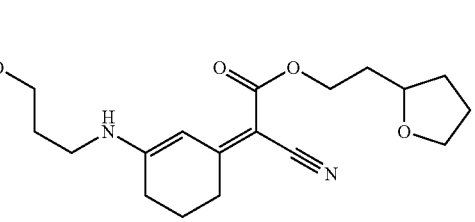 |
| 34 | 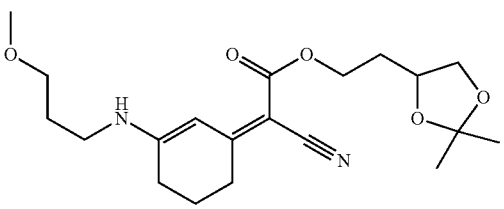 [SMILES: COCCCNC1=C/C(=C(/C#N)C(=O)OCCC2COC(C)(C)O2)CCC1] |
| 35 | 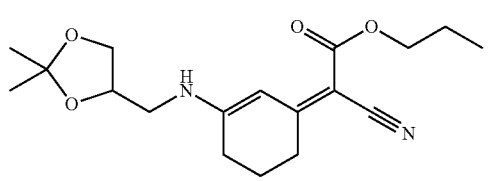 [SMILES: CCCOC(=O)/C(C#N)=C1\C=C(NCC2COC(C)(C)O2)CCC1] |

TABLE A-continued
| Compound | Structure |
|---|---|
| 36 | 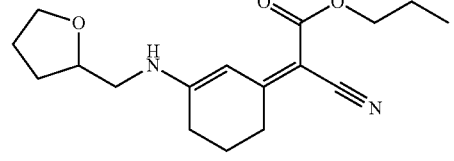 |
| 37 | 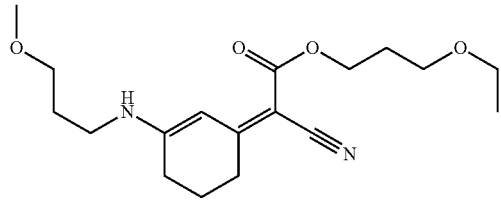 [SMILES: CCOCCCOC(=O)/C(C#N)=C1\C=C(NCCCOC)CCC1] |
| 38 | 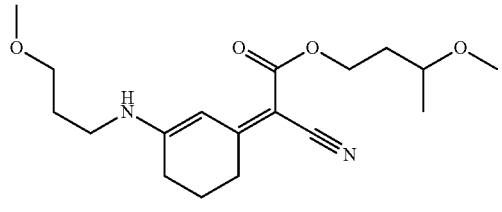 [SMILES: COCCCNC1=C/C(=C(/C#N)C(=O)OCCC(C)OC)CCC1] |
| 39 | 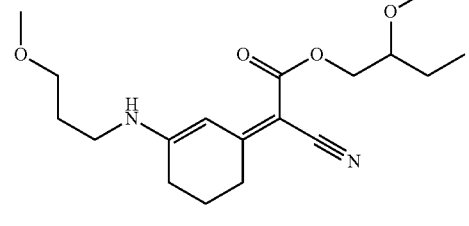 |
| 40 | 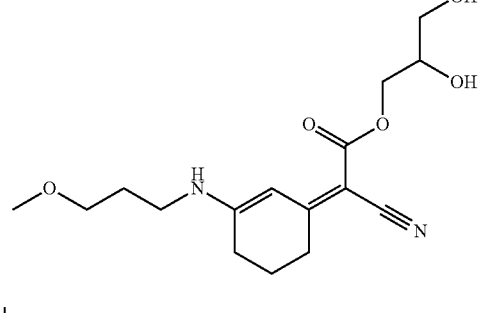 |
| 41 | 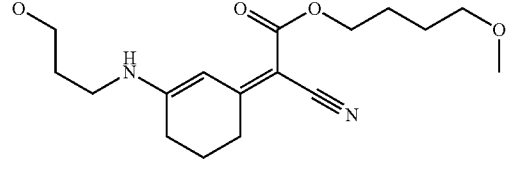 |
| 42 | 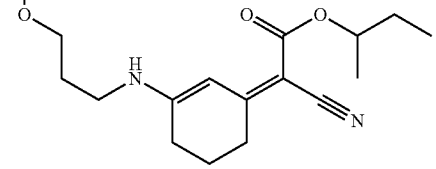 |

TABLE A-continued

| Compound | Structure |
|---|---|
| 43 | (structure: 3-hydroxypropyl ester of 2-cyano-2-[3-(3-methoxypropylamino)cyclohex-2-en-1-ylidene]acetate) |
| 44 | (structure: 2-hydroxyethyl ester of 2-cyano-2-[3-(3-methoxypropylamino)cyclohex-2-en-1-ylidene]acetate) |
| 45 | (structure: 2-(2-ethoxypropoxy)propyl ester of 2-cyano-2-[3-(3-methoxypropylamino)cyclohex-2-en-1-ylidene]acetate) |
| 46 | (structure: 2-[2-(2-ethoxypropoxy)propoxy]propyl ester variant of 2-cyano-2-[3-(3-methoxypropylamino)cyclohex-2-en-1-ylidene]acetate) |
| 47 | (structure: 2-[2-(2-ethoxypropoxy)propoxy]propyl ester variant of 2-cyano-2-[3-(3-methoxypropylamino)cyclohex-2-en-1-ylidene]acetate) |

The most preferred merocyanines derivatives of the invention are selected in the group of the following compounds and their E/E-, E/Z- or Z/Z geometrical isomer forms:

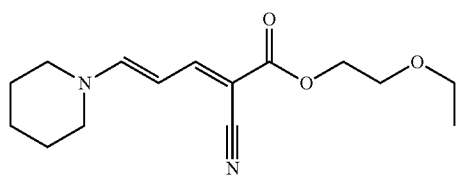

2-ethoxyethyl (2E,4E)-2-cyano-5-(piperidin-1-yl)penta-2,4-dienoate

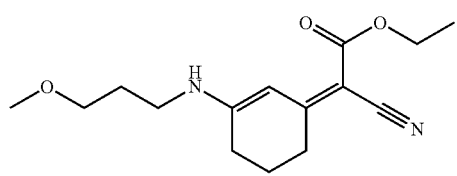

ethyl (2Z)-cyano{3-[(3-methoxypropyl)amino]cyclohex-2-en-1-ylidene}ethanoate

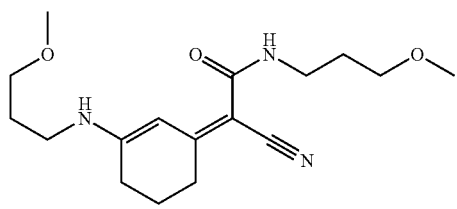

(2Z)-2-cyano-N-(3-methoxypropyl)-2-{3-[(3-methoxypropyl)amino]cyclohex-2-en-1-ylidene}ethanamide

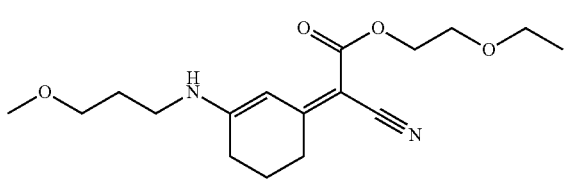 [SMILES: CCOCCOC(=O)/C(C#N)=C1\C=C(NCCCOC)CCC1]

2-ethoxyethyl (2Z)-cyano{3-[(3-methoxypropyl)amino]cyclohex-2-en-1-ylidene}ethanoate

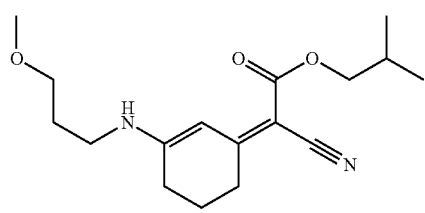

2-methylpropyl (2Z)-cyano{3-[(3-methoxypropyl)amino]cyclohex-2-en-1-ylidene}ethanoate

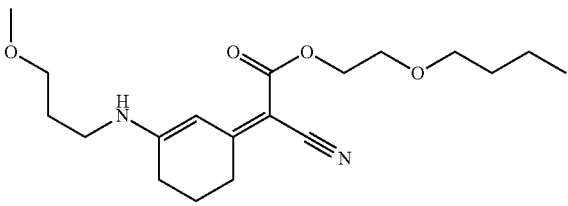

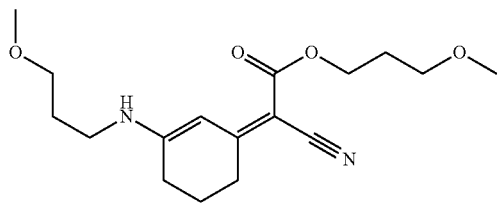

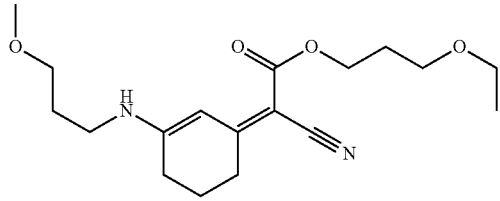

According to a preferred embodiment of the invention, the compound 2-ethoxyethyl (2Z)-cyano{3-[(3-methoxypropyl)amino]cyclohex-2-en-1-ylidene}ethanoate (25) in its E/E and/or its E/Z geometrical isomer forms will be used.

The E/Z form has the following structure

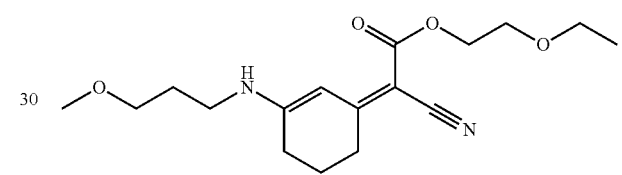

The E/E form has the following structure

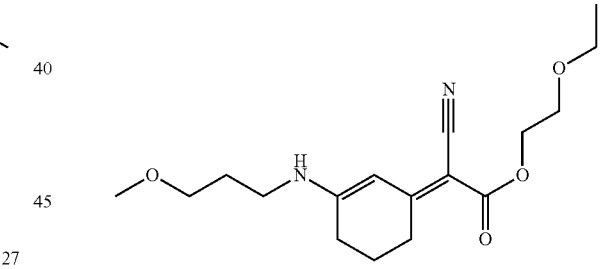

The Applicant discovered that those particular compounds have the following properties: better chemical stability after 2 months at 45° C. in ethanol/water 1/1 mixture at 0.5% of concentration, a less yellow coloring.

The merocyanine screening agent(s) in accordance with the invention may be present in the compositions according to the invention in a concentration from 0.1% to 10% and preferably from 0.2% to 5% by weight relative to the total weight of the composition The compounds of formula (1) and (2) may be prepared according to known processes, as disclosed for example in J. Org. Chem. USSR (Engl. Transl.) 26(8), p. 1562f (1990); J. Heterocycl. Chem. 33(3), p. 763-766 (1996); Khimiya Geterotsiklicheskikh Soedinenii 11, p. 1537-1543 (1984); Khimiya Geterotsiklicheskikh Soedinenii 3, p. 397-404 (1982); Chem. Heterocycl. Comp. (Engl. Transl.) 24(8), 914-919 (1988) and in Synthetic Communications Vol. 33, No. 3, 2003, p 367-371.

The synthesis of the compounds used in the present invention is also disclosed in US2003/0181483A1, WO 0234710, Eur. J. Org. Chem. 2003, 2250-2253, J. Med. Chem. 1996, 39, 1112-1124 and J. Org. Chem., Vol. 37, No. 8, 1972, 1141-1145 as follows:

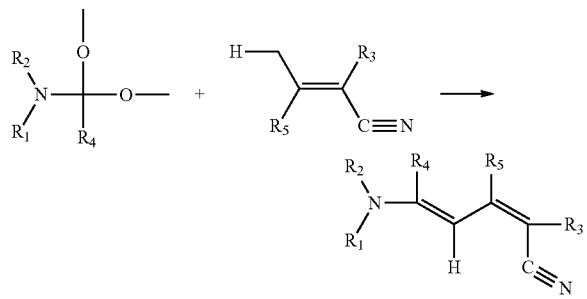

Vinylogene CH-acid compounds are reacted with acetales of amides.

In J. Heterocyclic Chem., 27, 1990, 1143-1151 aminoacrylic acid esters or aminoacrylnitriles are reacted with ethoxymethylenecyanoacetates in ethanol to the corresponding compounds used in the present invention.

Compounds of formula (1) and (2) wherein $R_4$ and $R_5$ or $R_9$ and $R_{10}$ together form a carbocyclic ring containing 6 C atoms, respectively, may be prepared according to procedures described in Pat. Appl. WO 2007/071582, in IP.com Journal (2009), 9(5A), 29-30 under the title "Process for producing 3-amino-2-cyclohexan-1-ylidene compounds" and in U.S. Pat. No. 4,749,643 on col, 13, line 66-col. 14, line 57 and the references cited therein.

The merocyanines of formula:

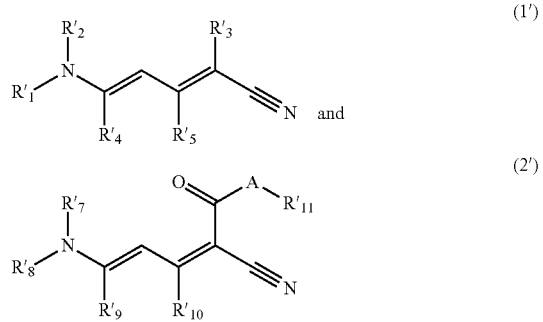

$R'_1$ and $R'_2$ independently of each other are hydrogen; $C_1$-$C_{22}$alkyl, $C_2$-$C_{22}$alkenyl, $C_2$-$C_{22}$alkinyl, which are optionally substituted by at least one hydroxy; or $R'_1$ and $R'_2$ together with the nitrogen atom linking them form a —($CH_2$)n- ring which is optionally interrupted by —O— or by —NH—;

$R'_3$ is a —(C=O)$OR'_6$ group; or a —(CO)$NHR'_6$ group;

$R'_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;

$R'_4$ and $R'_5$ are hydrogen; or $R'_4$ and $R'_5$ form a —($CH_2$)$_n$— ring which is optionally substituted by $C_1$-$C_4$alkyl and/or interrupted by —O— or by —NH—;

n is a number from 2 to 7;

$R'_7$ and $R'_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH; or $R'_7$ and $R'_8$ together with the nitrogen atom linking them form a —($CH_2$)n- ring which is optionally interrupted by —O—; $R'_9$ and $R'_{10}$ are hydrogen; or R'9 and R'10 form a —($CH_2$)$_n$— ring which is optionally substituted by $C_1$-$C_4$alkyl and/or optionally interrupted by —O— or by —NH—;

A is —O—; or —NH;

$R'_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally interrupted by one or more than one O;

are particularly suitable for protecting body care products from photolytic and oxidative degradation.

Preferably compounds of formula (1') or (2') are used wherein at least one of $R_1$, $R_2$, $R_3$ and $R_6$, $R_7$ and $R_8$, or R11 is substituted by hydroxy; and/or interrupted by one or more than one —O—.

Examples of compounds of formula (1') and (2') are those listed in Table A and the compound

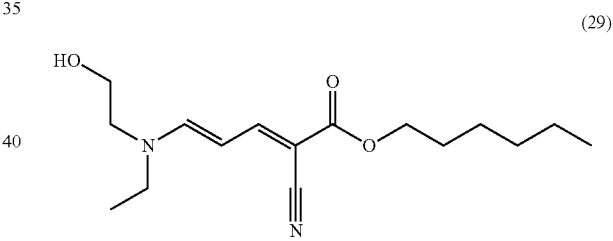

(29)

According to the invention, the compositions may further contain one or more complementary hydrophilic, lipophilic or insoluble organic screening agents and/or one or more inorganic screening agents which are active in UVA and/or UVB radiations.

Examples of complementary UV filters that can be used in admixture with the compounds of formulas (1) and (2) are listed in the following Tables:

TABLE 1

Suitable UV filter substances which can be additionally used with the compounds of formula (1) and/or (2)

p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;

TABLE 1-continued

Suitable UV filter substances which can be additionally used with the compounds of formula (1) and/or (2)

polymeric UV absorbers, for example the benzylidene malonate derivatives described in EP-A-709 080;
camphor derivatives, for example 3-(4'-methyl)benzylidene-bornan-2-one, 3-benzylidenebornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)). The primary particle size is an average of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

TABLE 2

Suitable UV filter substances which can be additionally used with the merocyanines of formula (1) and (2)

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on p 3-5; |
| DE 10331804 | T1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorph olino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |

TABLE 2-continued

Suitable UV filter substances which can be additionally used with the merocyanines of formula (1) and (2)

| | |
|---|---|
| EP 1 258 481 | Ex 1, pp 7,8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3,4,9,10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |

TABLE 2-continued

Suitable UV filter substances which can be additionally used with the merocyanines of formula (1) and (2)

| | |
|---|---|
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11; T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the compounds of formula (1) and/or (2)

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; Octocrylene | 6197-30-4 |
| 30 | 2-ethylhexyl 4-(dimethylamino)benzoate | 21245-02-3 |
| 32 | 2-ethylhexyl salicylate | 118-60-5 |
| 33 | Benzoic acid, 4,4',4''-(1,3,5-triazine-2,4,6-triyltriimino)tris-, tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |

TABLE 3-continued

Suitable UV filter substances and adjuvants which can be additionally used with the compounds of formula (1) and/or (2)

| No. | Chemical Name | CAS No. |
|---|---|---|
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethylbutyl)-phenol]; Tinosorb M | 103597-45-1 |
| 46 | 2,4-bis{[4-(2-ethylhexyloxy)-2-hydroxy]-phenyl}-6-(4-methoxy-phenyl)-(1,3,5)-triazine; Tinosorb S | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[[(1,1-dimethylethyl)amino]carbonyl]phenyl]amino]1,3,5-triazine-2,4-diyl]diimino]bis-, bis(2-ethylhexyl)ester; diethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 53 | 1-Dodecanaminium, N-[3-[[4-(dimethylamino)benzoyl]amino]-propyl]N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzene acetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 77 | Pentanenitrile, 2-[2,3-dihydro-5-methoxy-3,3-dimethyl-6-[(2-methyl-2-propenyl)oxy]-1H-inden-1-ylidene]-4,4-dimethyl-3-oxo- | 425371-15-9 |
| 78 | Pentanenitrile, 2-(2,3-dihydro-6-hydroxy-5-methoxy-3,3-dimethyl-1H-inden-1-ylidene)-4,4-dimethyl-3-oxo- | 425371-14-8 |
| 79 | Benzenepropanenitrile, α-(2,3-dihydro-3,3,5-trimethyl-1H-inden-1-ylidene)-β-oxo- | 425371-11-5 |
| 80 | Cyclohexanepropanenitrile, α-[5-(1,1-dimethylethyl)-2,3-dihydro-3,3-dimethyl-1H-inden-1-ylidene]-1-methyl-β-oxo- | 425371-10-4 |
| 81 | Pentanenitrile, 2-[6-(acetyloxy)-2,3-dihydro-5-methoxy-3,3-dimethyl-1H-inden-1-ylidene]-4,4-dimethyl-3-oxo- | 425371-09-1 |

TABLE 3-continued

Suitable UV filter substances and adjuvants which can be additionally used with the compounds of formula (1) and/or (2)

| No. | Chemical Name | CAS No. |
|-----|---------------|---------|
| 82 | Pentanenitrile, 2-[2,3-dihydro-5-methoxy-3,3-dimethyl-6-[2-methyl-3-[1,3,3,3-tetramethyl-1-[(trimethylsilyl)oxy]disiloxanyl]propoxy]-1H-inden-1-ylidene]-4,4-dimethyl-3-oxo- | 425371-08-0 |
| 83 | Pentanenitrile, 2-(2,3-dihydro-5-methoxy-3,3,6-trimethyl-1H-inden-1-ylidene)-4,4-dimethyl-3-oxo- | 425371-07-9 |
| 84 | Pentanenitrile, 4,4-dimethyl-3-oxo-2-(2,3,7,8-tetrahydro-8,8-dimethyl-6H-indeno[5,6-b]-1,4-dioxin-6-ylidene)- | 425371-06-8 |
| 85 | Pentanenitrile, 2-(2,3-dihydro-3,3,6-trimethyl-1H-inden-1-ylidene)-4,4-dimethyl-3-oxo- | 425371-05-7 |
| 86 | Pentanenitrile, 2-(2,3-dihydro-3,3,5,6-tetramethyl-1H-inden-1-ylidene)-4,4-dimethyl-3-oxo- | 425371-04-6 |
| 87 | Pentanenitrile, 2-(2,3-dihydro-5-methoxy-3,3,4,6-tetramethyl-1H-inden-1-ylidene)-4,4-dimethyl-3-oxo- | 425371-03-5 |
| 88 | Pentanenitrile, 2-(2,3-dihydro-5,6-dimethoxy-3,3-dimethyl-1H-inden-1-ylidene)-4,4-dimethyl-3-oxo- | 261356-13-2 |
| 89 | Benzoic Acid, 2-[4-(Diethylamino)-2-Hydroxybenzoyl]-, Hexyl Ester; UVINUL A+ | 302776-68-7 |
| 90 | 2-Ethylhexyl 4-methoxycinnamate; UVINUL MC 80 | 5466-77-3 |
| 91 | 2-Propenoic acid, 3-(4-methoxyphenyl)-, 3-methylbutyl ester; | 71617-10-2 |
| 92 | Phenol, 2-(2H-benzotriazol-2-yl)-6-dodecyl-4-methyl-; TINOGARD TL | 23328-53-2 |

Needless to say, a person skilled in the art will take care to select the optional additional screening agent(s) and/or the amounts thereof such that the advantageous properties intrinsically associated with the compositions in accordance with the invention are not, or are not substantially, adversely affected by the envisaged addition(s).

The additional organic screening agents are chosen more preferably from dibenzoylmethane derivatives; anthranilates; cinnamic derivatives; salicylic derivatives; camphor derivatives; benzophenone derivatives; β,β-diphenylacrylate derivatives; triazine derivatives; benzalmalonate derivatives, especially those mentioned in U.S. Pat. No. 5,624,663; benzimidazole derivatives; imidazolines; p-aminobenzoic acid (PABA) derivatives; benzotriazole derivatives; methylenebis-(hydroxyphenylbenzotriazole) derivatives as described in patent applications U.S. Pat. Nos. 5,237,071, 5,166,355, GB 2 303 549, DE 197 26 184 and EP 893 119; benzoxazole derivatives as described in patent applications EP 0 832 642, EP 1 027 883, EP 1 300 137 and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981; merocyanine derivatives such as those described in patent applications WO 04/006878, WO 05/058269 and WO 06/032741; the indanylidene screening agents of patents EP-A-0 823 418 and EP-A-1 341 752 and their mixtures.

As examples of organic UV-screening agents, mention may be made of those denoted hereinbelow under their INCI name:
Dibenzoylmethane Derivatives:
 Butylmethoxydibenzoylmethane, sold under the trade name Parsol 1789 by the company DSM Nutritional Products.
Para-Aminobenzoic Acid Derivatives:
 PABA,
 Ethyl PABA,
 Ethyl dihydroxypropyl PABA,
 Ethylhexyl dimethyl PABA sold in particular under the name Escalol 507 by ISP,
 Glyceryl PABA,
 PEG-25 PABA sold under the name Uvinul P25 by BASF,
Salicylic Derivatives:
 Homosalate sold under the name Eusolex HMS by Merck,
 Ethylhexyl salicylate sold under the name Neo Heliopan OS by Symrise,
 Dipropylene glycol salicylate sold under the name Dipsal by Lubrizol,
 TEA salicylate sold under the name Neo Heliopan TS by Symrise.
Cinnamic Derivatives:
 Ethylhexyl methoxycinnamate sold especially under the trade name Parsol MCX by DSM Nutritional Products,
 Isopropyl methoxycinnamate,
 Isoamyl methoxycinnamate sold under the trade name Neo Heliopan E 1000 by Symrise,
 Cinoxate,
 DEA Methoxycinnamate,
 Diisopropyl methylcinnamate,
 Glyceryl ethylhexanoate dimethoxycinnamate
β,β-Diphenylacrylate derivatives:
 Octocrylene sold especially under the trade name Uvinul N539 by BASF,
 Etocrylene sold especially under the trade name Uvinul N35 by BASF,
Benzophenone Derivatives:
 Benzophenone-1 sold under the trade name Uvinul 400 by BASF,
 Benzophenone-2 sold under the trade name Uvinul D50 by BASF,
 Benzophenone-3 or Oxybenzone sold under the trade name Uvinul M40 by BASF,
 Benzophenone-4 sold under the trade name Uvinul MS40 by BASF,
 Benzophenone-5,
 Benzophenone-6 sold under the trade name Helisorb 11 by Norquay,
 Benzophenone-8 sold under the trade name Cyasorb UV-24 by Cytec, Benzophenone-9 sold under the trade name Uvinul DS-49 by BASF, Benzophenone-12, n-hexyl 2-(4-diethylamino-2-hydroxybenzoyl)benzoate sold under the trade name Uvinul A+ or in the form of a mixture with octyl methoxycinnamate under the trade name Uvinul A+B by BASF, 1,1'-(1,4-piperazinediyl)bis[1-[2-[4-(diethylamino)-2-hydroxybenzoyl]phenyl]methanone (CAS 919803-06-8), Benzylidene Camphor Derivatives:

3-Benzylidenecamphor manufactured under the name Mexoryl SD by Chimex,

4-Methylbenzylidenecamphor sold under the name Eusolex 6300 by Merck,

Benzylidenecamphorsulfonic acid manufactured under the name Mexoryl SL by Chimex, Camphor benzalkonium methosulfate manufactured under the name Mexoryl SO by Chimex, Terephthalylidenedicamphorsulfonic acid manufactured under the name Mexoryl SX by Chimex, Polyacrylamidomethylbenzylidenecamphor manufactured under the name Mexoryl SW by Chimex, Phenylbenzimidazole Derivatives:

Phenylbenzimidazolesulfonic acid sold in particular under the trade name Eusolex 232 by Merck, Disodium phenyl dibenzimidazole tetrasulfonate sold under the trade name Neo Heliopan AP by Symrise.

Benzotriazole Derivatives:

Drometrizole trisiloxane sold under the name Silatrizole by Rhodia Chimie, Methylenebis(benzotriazolyl)tetramethylbutylphenol sold in solid form under the trade name MIXXIM BB/100 by Fairmount Chemical, or in micronized form as an aqueous dispersion under the trade name Tinosorb M by BASF.

Triazine Derivatives:

Bis(ethylhexyloxyphenol)methoxyphenyltriazine sold under the trade name Tinosorb S by BASF, Ethylhexyltriazone sold in particular under the trade name Uvinul T150 by BASF, Diethylhexylbutamidotriazone sold under the trade name Uvasorb HEB by Sigma 3V, The silicone triazine substituted by two aminobenzoates groups as those disclosed in the patent EP0841341 in particular the compound 2,4-Bis(n-butyl 4'-aminobenzalmalonate)-6-[(3-{1,3,3,3-tetramethyl-1-[(trimethylsilyloxy]disiloxanyl}propyl)amino]-s-triazine, 2,4,6-Tris(diisobutyl 4'-aminobenzalmalonate)-s-triazine, 2,4,6-Tris(dineopentyl 4'-aminobenzalmalonate)-s-triazine, 2,4-Bis(dineopentyl 4'-aminobenzalmalonate)-6-(n-butyl 4'-aminobenzoate)-s-triazine, the symmetrical triazine screening agents described in U.S. Pat. No. 6,225,467, patent application WO 2004/085412 (see compounds 6 and 9) or the document "Symmetrical Triazine Derivatives" IP.COM Journal, IP.COM INC West Henrietta, N.Y., US (20 Sep. 2004), especially 2,4,6-tris(biphenyl)-1,3,5-triazines (in particular 2,4,6-tris(biphenyl-4-yl-1,3,5-triazine) and 2,4,6-tris(terphenyl)-1,3,5-triazine which is also mentioned in Beiersdorf patent applications WO 06/035000, WO 06/034982, WO 06/034991, WO 06/035007, WO 2006/034992 and WO 2006/034985.

Anthranilic Derivatives:

Menthyl anthranilate sold under the trade name Neo Heliopan MA by Symrise,

Imidazoline Derivatives:

Ethylhexyl dimethoxybenzylidene dioxoimidazoline propionate,

Benzalmalonate Derivatives:

Dineopentyl 4'-methoxybenzalmalonate, Polyorganosiloxane containing benzalmalonate functions, for instance Polysilicone-15, sold under the trade name Parsol SLX by DSM Nutritional Products.

4,4-Diarylbutadiene Derivatives:

1,1-Dicarboxy(2,2'-dimethylpropyl)-4,4-diphenylbutadiene,

Benzoxazole Derivatives:

2,4-Bis[5-1(dimethylpropyl)benzoxazol-2-yl-(4-phenyl)imino]-6-(2-ethylhexyl)imino-1,3,5-triazine, and mixtures thereof.

The most preferential additional organic screening agents are chosen from:

Ethylhexyl methoxycinnamate,
Homosalate,
Ethylhexyl salicylate,
Octocrylene,
Butylmethoxydibenzoylmethane
Terephthalylidenedicamphorsulfonic acid,
Disodium phenyldibenzimidazoletetrasulfonate,
Phenylbenzimidazolesulfonic acid,
Benzophenone-3,
n-Hexyl 2-(4-diethylamino-2-hydroxybenzoyl)benzoate,
4-Methylbenzylidenecamphor,
Ethylhexyl triazone,
Bis(ethylhexyloxyphenol)methoxyphenyltriazine,
Diethylhexyl Butamidotriazone,
2,4-Bis(n-butyl 4'-aminobenzalmalonate)-6-[(3-{1,3,3,3-tetramethyl-1-[(trimethylsilyl)-oxy]disiloxanyl}propyl)amino]-s-triazine,
2,4,6-Tris(biphenyl-4-yl-1,3,5-triazine,
2,4,6-Tris(dineopentyl 4'-aminobenzalmalonate)-s-triazine,
2,4,6-Tris(diisobutyl 4'-aminobenzalmalonate)-s-triazine,
2,4-Bis(dineopentyl 4'-aminobenzalmalonate)-6-(n-butyl 4'-aminobenzoate)-s-triazine,
Methylenebis(benzotriazolyl)tetramethylbutylphenol,
Drometrizole trisiloxane,
Polysilicone-15,
Dineopentyl 4'-methoxybenzalmalonate,
1,1-Dicarboxy(2,2'-dimethylpropyl)-4,4-diphenylbutadiene,
2,4-Bis[5-1(dimethylpropyl)benzoxazol-2-yl-(4-phenyl)imino]-6-(2-ethylhexyl)imino-1,3,5-triazine,
and mixtures thereof.

The additional organic UV-screening agents are preferably present in the compositions according to the invention in proportions ranging from 0.01% to 20% by weight relative to the total weight of the composition, and preferably ranging from 0.1% to 15% by weight relative to the total weight of the composition.

The additional mineral screening agents are chosen from coated or uncoated metal oxide pigments in which the mean size of the primary particles is preferentially between 5 nm and 100 nm (preferably between 10 nm and 50 nm), for instance titanium oxide (amorphous or crystallized in rutile and/or anatase form), iron oxide, zinc oxide, zirconium oxide or cerium oxide pigments, which are all UV-photoprotective agents that are well known per se.

The pigments may be coated or uncoated.

The coated pigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and consist essentially of a repetition of main units in which the silicon atoms are linked together via oxygen atoms (siloxane bond), optionally substituted hydrocarbon-based radicals being directly attached via a carbon atom to the said silicon atoms.

The term "silicones" also includes the silanes required for their preparation, in particular alkylsilanes.

The silicones used for the coating of the pigments suitable for the present invention are preferably chosen from the group consisting of alkylsilanes, polydialkylsiloxanes and polyalkylhydrosiloxanes. More preferably still, the silicones are chosen from the group containing octyltrimethylsilane, polydimethylsiloxanes and polymethylhydrosiloxanes.

Of course, before being treated with silicones, the metal oxide pigments may have been treated with other surface agents, in particular with cerium oxide, alumina, silica, aluminium compounds or silicon compounds, or mixtures thereof.

Such metal oxide pigments, coated or non coated are in particular disclosed in the patent application EP-A-0 518 773. As commercial pigments, we can mention the products sold by the companies Sachtleben, Tayca, Merck et Evonik.

The coated pigments are more particularly titanium oxides that have been coated:
  with silica, such as the product Sunveil from the company Ikeda and the product Eusolex T-AVO from the company Merck,
  with silica and iron oxide, such as the product Sunveil F from the company Ikeda,
  with silica and alumina, such as the products Microtitanium Dioxide MT 500 SA and Microtitanium Dioxide MT 100 SA from the company Tayca, Tioveil from the company CRODA and Mirasun TiW 60 from the company Rhodia,
  with alumina, such as the products Tipaque TTO-55 (B) and Tipaque TTO-55 (A) from the company Ishihara and UVT 14/4 from the company Kemira,
  with alumina and aluminium stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Croda,
  with alumina and aluminium stearate, such as the product Microtitanium Dioxide MT 100 TV, MT 100 TX, MT 100 Z and MT-01 from the company Tayca, and the products Solaveil CT-10 W, Solaveil CT 100 and Solaveil CT 200 from the company Croda,
  with silica, alumina and alginic acid, such as the product MT-100 AQ from the company Tayca,
  with alumina and aluminium laurate, such as the product Microtitanium Dioxide MT 100 S from the company Tayca,
  with iron oxide and iron stearate, such as the product Microtitanium Dioxide MT 100 F from the company Tayca,
  with zinc oxide and zinc stearate, such as the product BR351 from the company Tayca,
  with silica and alumina and treated with a silicone, such as the products Microtitanium Dioxide MT 600 SAS, Microtitanium Dioxide MT 500 SAS or Microtitanium Dioxide MT 100 SAS from the company Tayca,
  with silica, alumina and aluminium stearate and treated with a silicone, such as the product STT-30-DS from the company Titan Kogyo,
  with silica and treated with a silicone, such as the product UV-Titan M 195 from the company Sachtleben, or the product SMT-100 WRS from the company Tayca,
  with alumina and treated with a silicone, such as the products Tipaque TTO-55 (S) from the company Ishihara or UV Titan M 262 from the company Sachtleben,
  with triethanolamine, such as the product STT-65-S from the company Titan Kogyo,
  with stearic acid, such as the product Tipaque TTO-55 (C) from the company Ishihara,
  with sodium hexametaphosphate, such as the product Microtitanium Dioxide MT 150 W from the company Tayca.
  treated with octyl triméthyl silane such as the product <<T 805>> from the company EVONIK,
  treated with a polydiméthyl siloxane such as the product <<70250 Cardre UF TiO2SI3>> from the company CARDRE,
  anatase/rutile $TiO_2$ treated with a polydiméthylhydrogénosiloxane such as the product <<MICRO TITANIUM DIOXYDE USP GRADE HYDROPHOBIC>> from the company COLOR TECHNIQUES.

The uncoated titanium oxide pigments are sold, for example, by the company Tayca under the trade names "Microtitanium Dioxide MT 500 B" or "Microtitanium Dioxide MT 600 B", by the company EVONIK under the name P 25, by the company Wacker under the name Transparent titanium oxide PW, by the company Miyoshi Kasei under the name UFTR, by the company Tomen under the name ITS and by the company CRODA under the name Tioveil AQ.

The uncoated zinc oxide pigments are, for example:
  those sold under the name Z-Cote by the company Sunsmart;
  those sold under the name Nanox by the company Elementis;
  those sold under the name Nanogard WCD 2025 by the company Nanophase Technologies.

The coated zinc oxide pigments are, for example:
  those sold under the name Z-Cote HP1 by the company Sunsmart (dimethicone-coated ZnO);
  those sold under the name Zinc Oxide CS-5 by the company Toshibi (ZnO coated with polymethylhydrosiloxane);
  those sold under the name Nanogard Zinc Oxide FN by the company Nanophase Technologies (as a 40% dispersion in Finsolv TN, C12-C15 alkyl benzoate);
  those sold under the name Daitopersion ZN-30 and Daitopersion ZN-50 by the company Daito (dispersions in cyclopolymethylsiloxane/oxyethylenated polydimethyl-siloxane, containing 30% or 50% of nanozinc oxides coated with silica and polymethylhydrosiloxane);
  those sold under the name NFD Ultrafine ZnO by the company Daikin (ZnO coated with perfluoroalkyl phosphate and copolymer based on perfluoroalkylethyl as a dispersion in cyclopentasiloxane);
  those sold under the name SPD-Z1 by the company Shin-Etsu (ZnO coated with silicone-grafted acrylic polymer, dispersed in cyclodimethylsiloxane);

those sold under the name Escalol Z100 by the company ISP (alumina-treated ZnO dispersed in the ethylhexyl methoxycinnamate/PVP-hexadecene/methicone copolymer mixture);

those sold under the name Fuji ZnO-SMS-10 by the company Fuji Pigment (ZnO coated with silica and polymethylsilsesquioxane);

those sold under the name Nanox Gel TN by the company Elementis (ZnO dispersed at a concentration of 55% in C12-C15 alkyl benzoate with hydroxystearic acid polycondensate).

The uncoated cerium oxide pigments are sold, for example, under the name Colloidal Cerium Oxide by the company RHODIA.

The uncoated iron oxide pigments are sold, for example, by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220, The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name TRANSPARENT IRON OXIDE.

Mention may also be made of mixtures of metal oxides, especially of titanium dioxide and of cerium dioxide, including the silica-coated equal-weight mixture of titanium dioxide and of cerium dioxide, sold by the company IKEDA under the name Sunveil A, and also the alumina, silica and silicone-coated mixture of titanium dioxide and of zinc dioxide, such as the product M 261 sold by the company SACHTLEBEN, or the alumina, silica and glycerol-coated mixture of titanium dioxide and of zinc dioxide, such as the product M 211 sold by the company SACHTLEBEN.

According to the invention, coated or uncoated titanium oxide pigments are particularly preferred.

The inorganic UV filters according represents generally from 0.5 to 40%, preferably from 1 to 30%, by weight relating to the total weight of the composition.

According to their lipophilic character or their hydrophilic character, more or less pronounced, inorganic UV filters may be present in the oily phase, in the aqueous phase or in the two phases in an emulsion.

A particular form of the present invention relates to a composition comprising in a cosmetically acceptable medium at least one merocyanine derivative of formula (1) or (2) and at least one dibenzoylmethane derivative.

Among the dibenzoylmethane derivatives that may especially be mentioned, in a non-limiting manner, are:
2-methyldibenzoylmethane,
4-methyldibenzoylmethane,
4-isopropyldibenzoylmethane,
4-tert-butyldibenzoylmethane,
2,4-dimethyldibenzoylmethane,
2,5-dimethyldibenzoylmethane,
4,4'-diisopropyldibenzoylmethane,
4,4'-dimethoxydibenzoylmethane,
4-tert-butyl-4'-methoxydibenzoylmethane,
2-methyl-5-isopropyl-4'-methoxydibenzoylmethane,
2-methyl-5-tert-butyl-4'-methxydibenzoylmethane,
2,4-dimethyl-4'-methoxydibenzoylmethane,
2,6-dimethyl-4-tert-butyl-4'-methoxydibenzoylmethane.

It is most particularly preferred to use 4-(tert-butyl)-4'-methoxydibenzoylmethane or Butyl Methoxy Dibenzoylmethane or Avobenzone, sold under the trade name Parsol 1789 by the company DSM Nutritional Products, Inc.; this screening agent corresponds to the following formula:

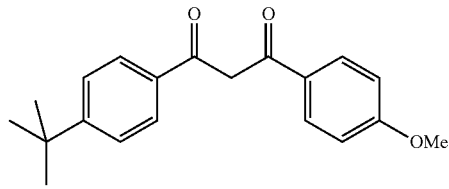 [SMILES: COc1ccc(C(=O)CC(=O)c2ccc(C(C)(C)C)cc2)cc1]

The dibenzoylmethane derivative(s) may be present in the compositions in accordance with the invention in contents preferably ranging from 0.01% to 20% by weight, more preferentially from 0.1% to 10% by weight and even more preferentially from 0.1% to 6% by weight relative to the total weight of the composition.

A particular form of the present invention relates to a composition comprising in a cosmetically acceptable medium at least the compound 2-ethoxyethyl (2Z)-cyano{3-[(3-methoxypropyl)amino]cyclohex-2-en-1-ylidene}ethanoate (25) in its E/E and/or E/Z geometrical isomer forms and a dibenzoylmethane derivative as above defined and particularly the 4-(tert-butyl)-4'-methoxydibenzoylmethane or Butyl Methoxy Dibenzoylmethane or Avobenzone.

The aqueous compositions in accordance with the present invention may also comprise standard cosmetic adjuvants chosen especially from fatty substances, organic solvents, ionic or nonionic, hydrophilic or lipophilic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents or any other ingredient usually used in cosmetics and/or dermatology.

The fatty substances may consist of an oil or a wax other than the apolar waxes as defined above, or mixtures thereof. The term oil means a compound that is liquid at room temperature. The term wax means a compound that is solid or substantially solid at room temperature and whose melting point is generally greater than 35° C.

Oils that may be mentioned include mineral oils (paraffin); plant oils (sweet almond oil, macadamia oil, blackcurrant seed oil or jojoba oil); synthetic oils, for instance perhydrosqualene, fatty alcohols, fatty amides (for instance isopropyl lauroyl sarcosinate sold under the name Eldew SL-205 by the company Ajinomoto), fatty acids or fatty esters, for instance the $C_{12}$-$C_{15}$ alkyl benzoate sold under the trade name Finsolv TN or Witconol TN by the company Witco, 2-ethylphenyl benzoate, for instance the commercial product sold under the name X-Tend 226® by the company ISP, octyl palmitate, isopropyl lanolate, diisopropyl sebacate sold under the trade name Dub Dis by the company Stearinerie Dubois and triglycerides, including capric/caprylic acid triglycerides, and dicaprylyl carbonate sold under the name Cetiol CC by the company Cognis, oxyethylenated or oxypropylenated fatty esters and ethers; silicone oils (cyclomethicone and polydimethylsiloxanes, or PDMS) or fluoro oils, polyalkylenes, and trialkyl trimellitates such as tridecyl trimellitate.

Waxy compounds that may be mentioned include carnauba wax, beeswax, hydrogenated castor oil, polyethylene waxes and polymethylene waxes, for instance the product sold under the name Cirebelle 303 by the company Sasol.

Among the organic solvents that may be mentioned are lower alcohols and polyols. These polyols may be chosen from glycols and glycol ethers, for instance ethylene glycol, propylene glycol, butylene glycol, caprylyl glycol, pentyleneglycol, dipropylene glycol or diethylene glycol.

A particularly interesting family of solvents that may be also mentioned includes the 4-carboxy-2-pyrrolidinone ester derivatives of formula (I), alone or as a mixture, and/or a salt and/or isomer and/or solvate thereof:

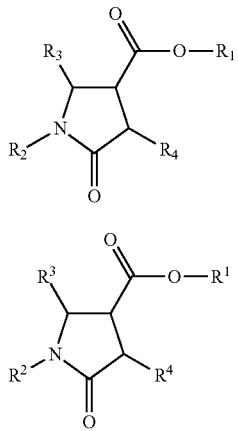

in which:
- $R^1$ denotes a hydrogen atom or a linear $C_1$-$C_{20}$ or branched $C_3$-$C_{20}$ alkyl radical;
- $R^2$ denotes a linear $C_1$-$C_{20}$ or branched $C_3$-$C_{20}$ alkyl radical which can contain a $C_5$-$C_6$ ring; a $C_5$-$C_6$ cycloalkyl radical optionally substituted with one or two methyl radicals; the phenyl radical, the benzyl radical or the phenethyl radical;
- $R^3$ and $R^4$ denote, independently of one another, a hydrogen atom, or a linear $C_1$-$C_{12}$ or branched $C_3$-$C_{12}$ alkyl radical;

it being understood that, when $R^1$=H, the compounds may be in their free acid form or in the form of their cosmetically acceptable salts.

In formula (I), among the alkyl groups, mention may in particular be made of methyl, ethyl, n-propyl, isopropyl, n-butyl, isobutyl, tert-butyl, n-octyl, 2-ethylhexyl, dodecyl, hexadecyl, cyclohexyl or methylcyclohexyl groups.

The salts of the compounds described in the present invention comprise the conventional nontoxic salts of said compounds, such as those formed from cosmetically acceptable organic or inorganic acids or bases. Mention may be made of ammonium salts, alkanolamine salts such as triethanolamine salts, aminopropanediol salts, and salts of alkali metals or alkaline-earth metals, such as sodium, potassium, magnesium and calcium.

The preferred compounds are those of formula (I) in which $R^3$ and $R^4$ are hydrogen.

Preferably, $R^1$ denotes a hydrogen atom or a linear $C_1$-$C_{18}$ or branched $C_3$-$C_{18}$ alkyl radical; and better still a linear $C_2$-$C_{18}$ or branched $C_3$-$C_{10}$ alkyl radical.

Preferably, $R^2$ denotes a linear $C_2$-$C_{18}$ or branched $C_3$-$C_{18}$ alkyl radical; and better still a linear $C_3$-$C_{16}$ or branched $C_3$-$C_{12}$ alkyl radical; or a cyclohexyl, phenyl, benzyl or phenethyl radical; most preferably, $R^2$ denotes a linear $C_4$-$C_{10}$ or branched $C_4$-$C_{10}$ alkyl radical; such as butyl and 2-ethylhexyl.

Among the compounds of formula (I), use will more particularly be made of the following products (a) to (bx):

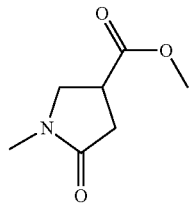

(a)

RN = 59857-86-2

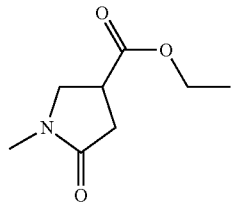

(b)

RN = 10080-92-9

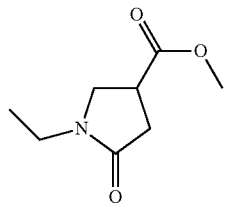

(c)

RN = 100911-29-3

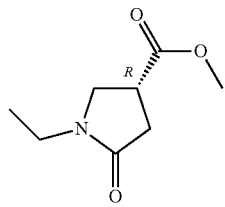

(d)

RN = 428518-32-5

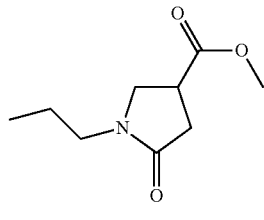

(e)

RN = 102903-44-2

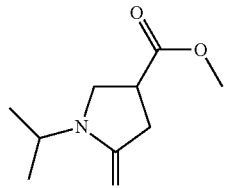

(f)

RN = 59857-84-0

(g)
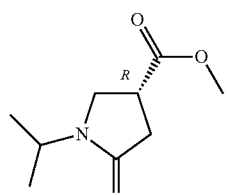
RN = 428518-33-6
(h)
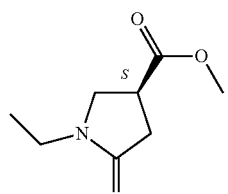
R = 443304-01-6
(i)
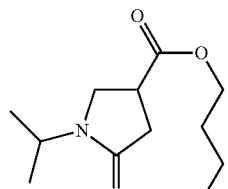
RN = 100453-61-0
(j)
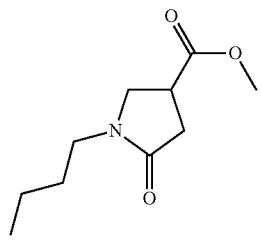
RN = 59857-87-3
(k)
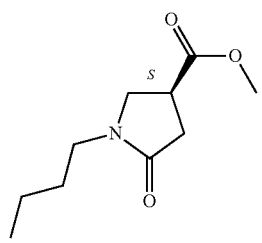
RN = 428518-34-7
(l)
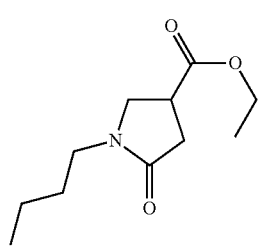
RN = 192717-78-5
(m)
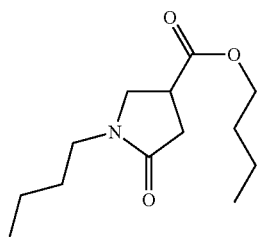
(n)
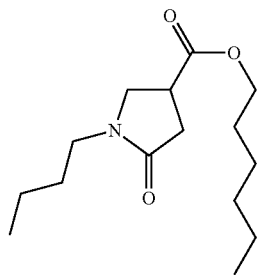
RN = 856637-16-6
(o)
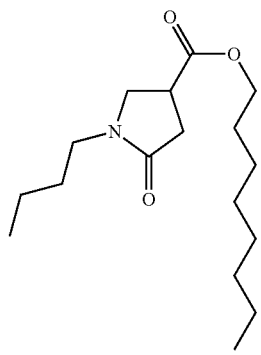
RN = 101572-83-2
(p)
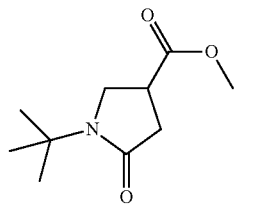
RN = 59857-85-1
(q)
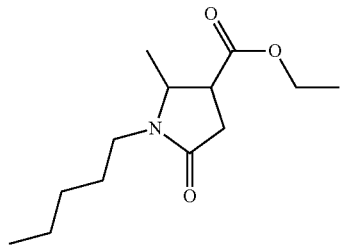
RN = 873969-57-4

(r) 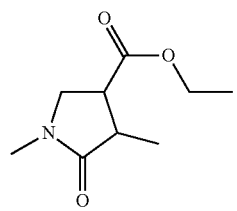
RN = 60298-19-3
(s) 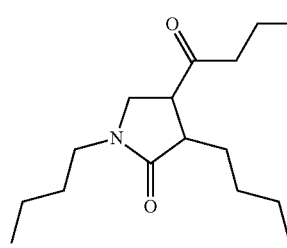
(t) 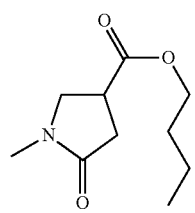
RN = 593253-22-6
(u) 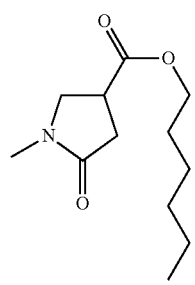
(v) 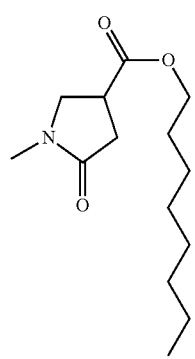
(w) 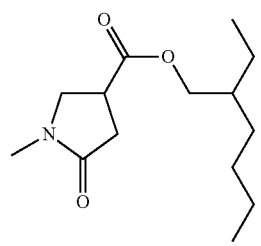
(x) 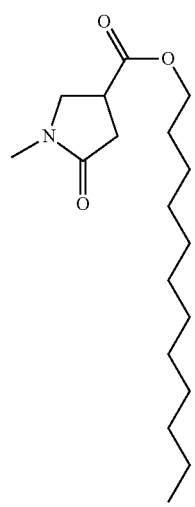
(y) 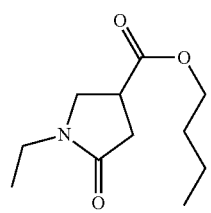
(z) 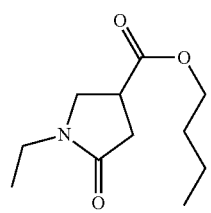
(aa) 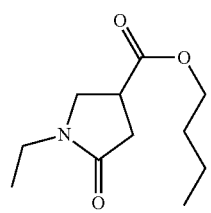

-continued
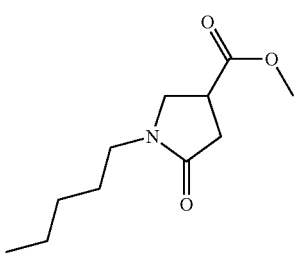
RN = 147452-59-3
(ab)
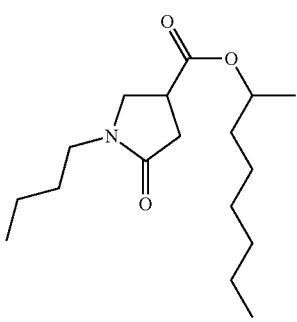
(ac)
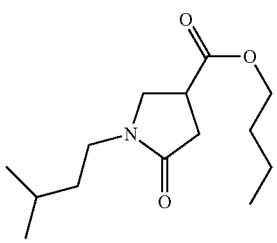
RN = 100878-04-4
(ad)
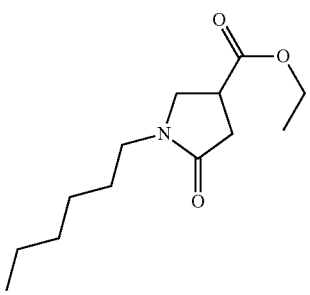
(ae)
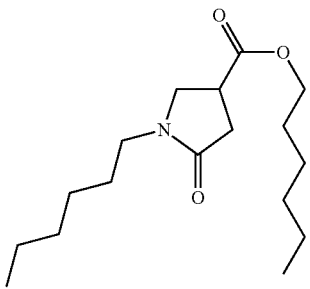
RN = 856636-64-1
-continued
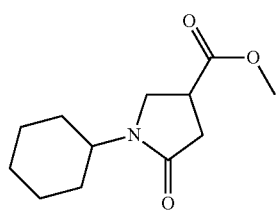
RN = 100252-83-3
(ag)
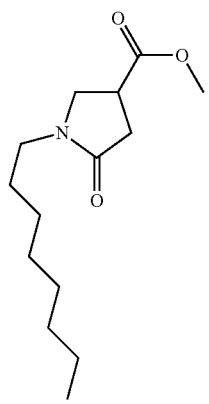
RN = 106783-22-6
(ah)
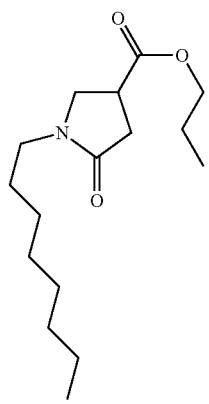
RN = 66397-80-6
(ai)
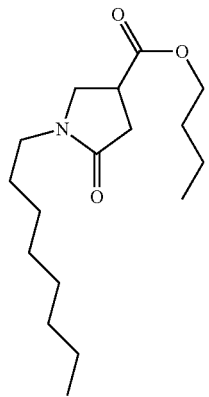
RN = 101572-84-3
(aj)

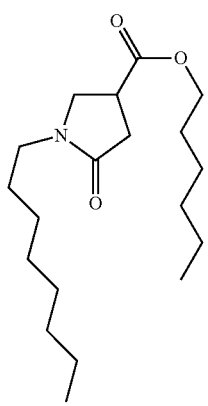
RN = 102180-23-4
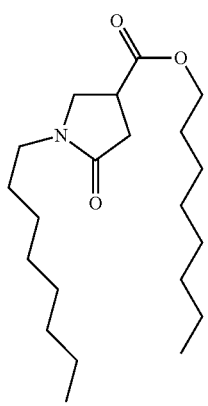
RN = 102444-77-9
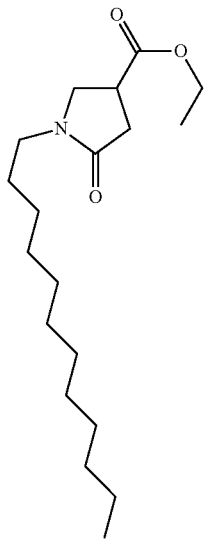
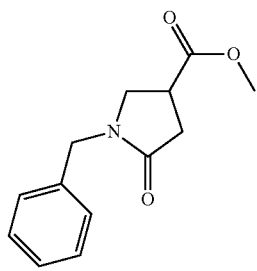
(ak)
RN = 51535-00-3
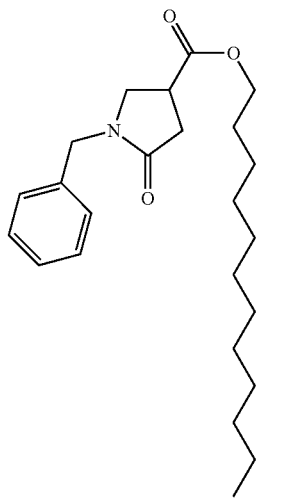
(al)
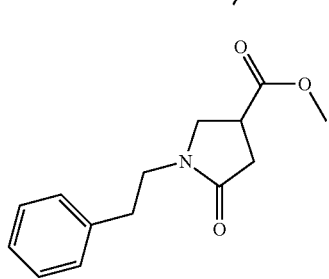
(ap)
RN = 100718-54-5
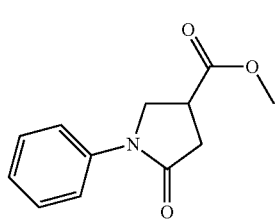
(aq)
RN = 64320-92-9
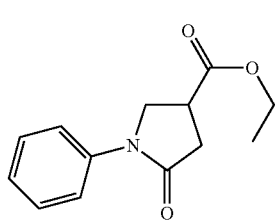
(ar)
RN = 91957-98-1

51
-continued
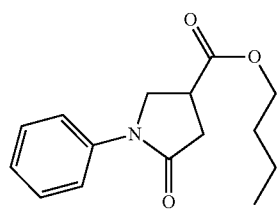
(as)
RN = 101105-62-8
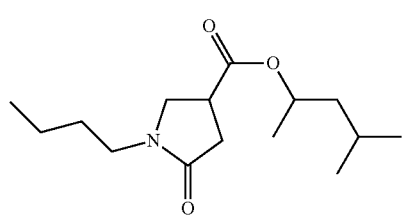
(at)
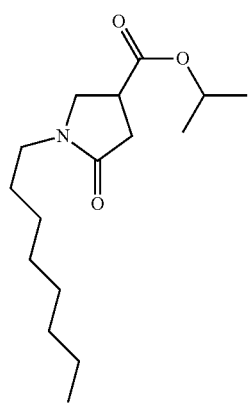
(au)
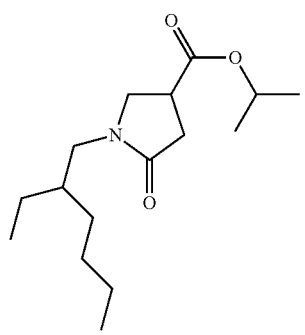
(av)
52
-continued
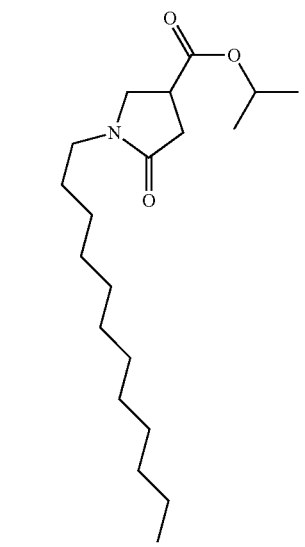
(aw)
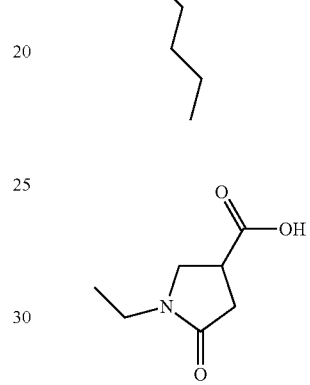
(ax)
RN = 52743-73-4
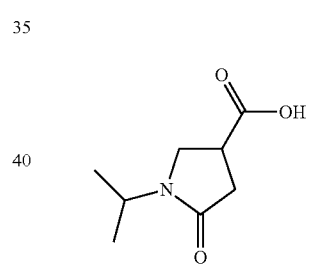
(ay)
RN = 299920-47-1
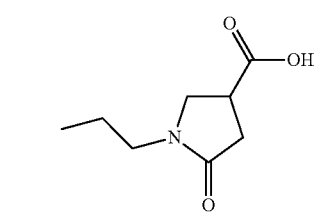
(az)
RN = 208118-23-4
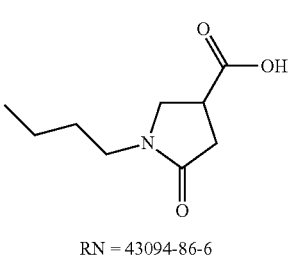
(ba)
RN = 43094-86-6

(bb)
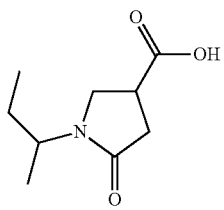
RN = 696647-92-4
(bc)
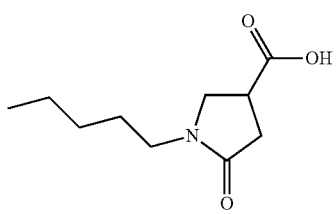
RN = 845546-13-6
(bd)
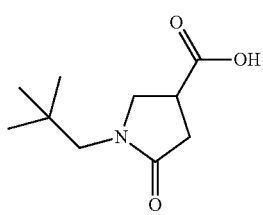
RN = 157687-77-9
(be)
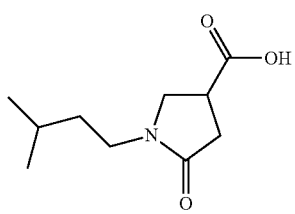
RN = 944648-73-1
(bf)
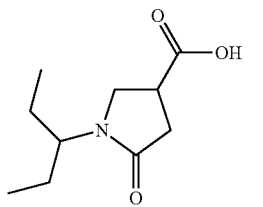
RN = 944511-54-0
(bg)
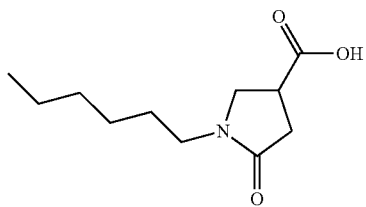
RN = 116167-27-2
(bh)
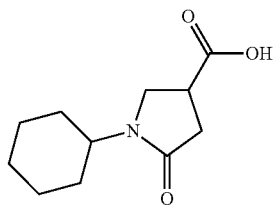
RN = 6304-56-9
(bi)
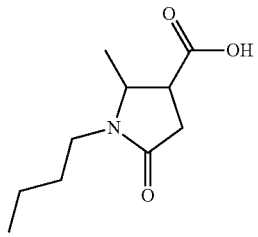
(bj)
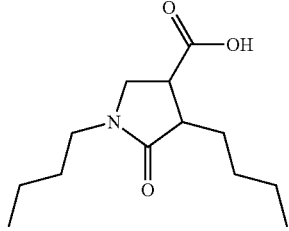
(bk)
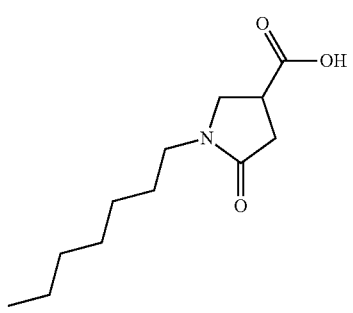
RN = 944683-34-5
(bl)
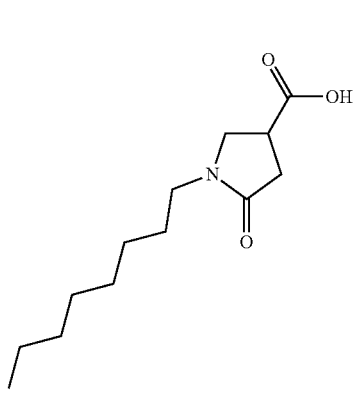
RN = 58505-91-2

-continued
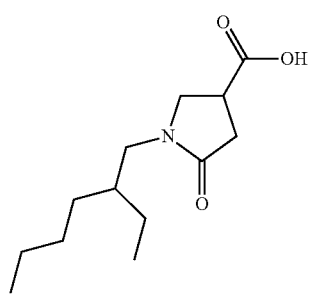
RN = 1211449-66-9
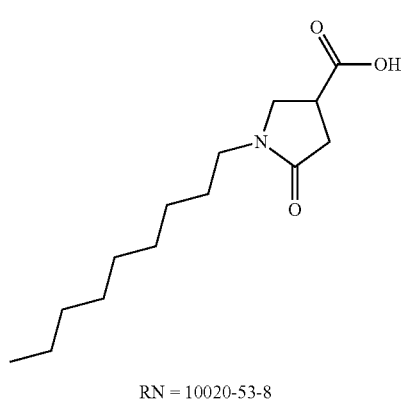
RN = 10020-53-8
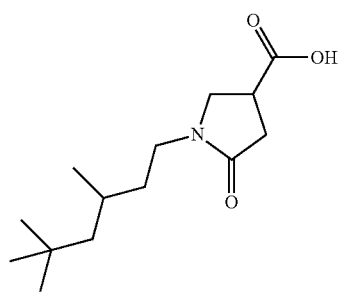
RN = 857424-96-5
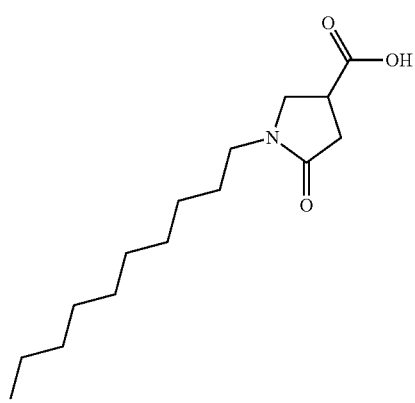
RN = 94108-37-9
-continued
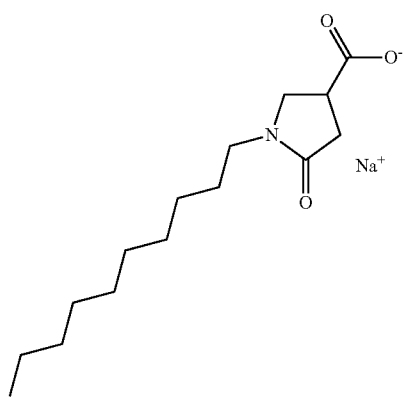
RN = 116008-24-3
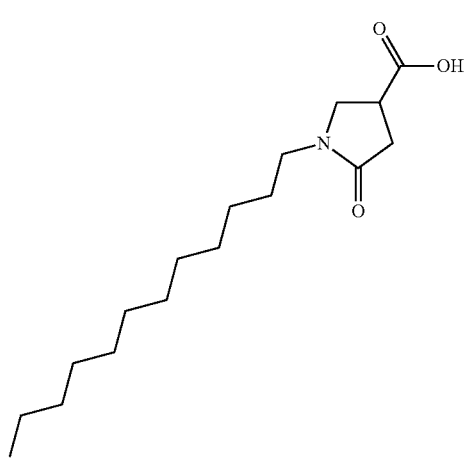
RN = 10054-21-4
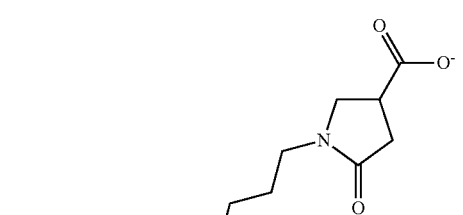
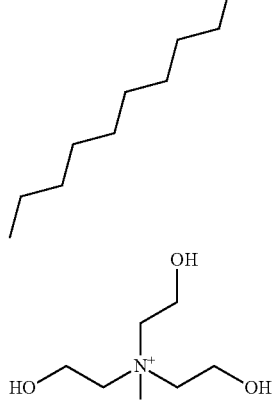
RN = 94108-39-1

(bt)

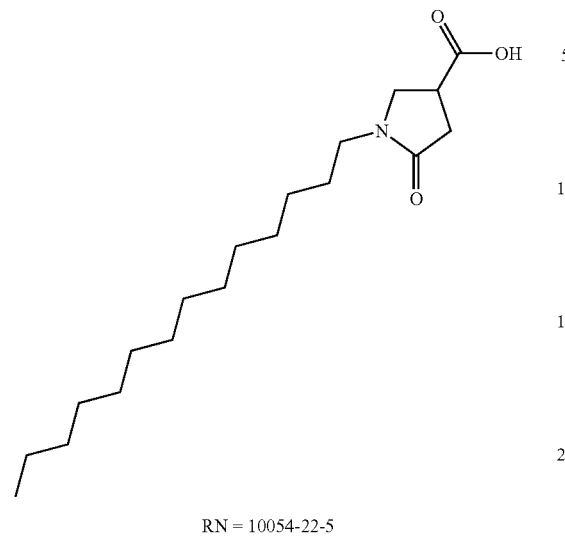

RN = 10054-22-5

(bu)

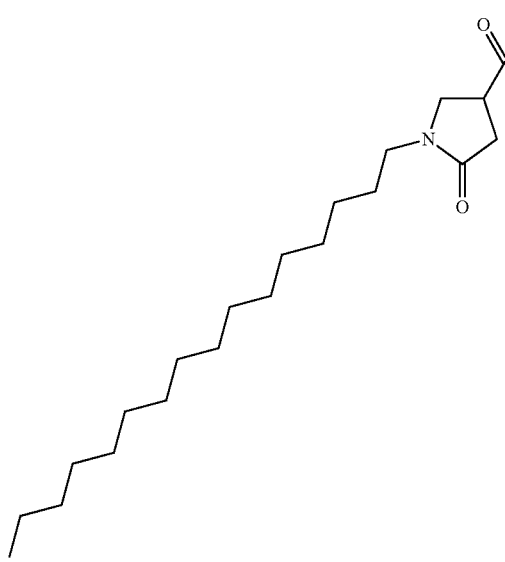

RN = 10054-19-0

(bv)

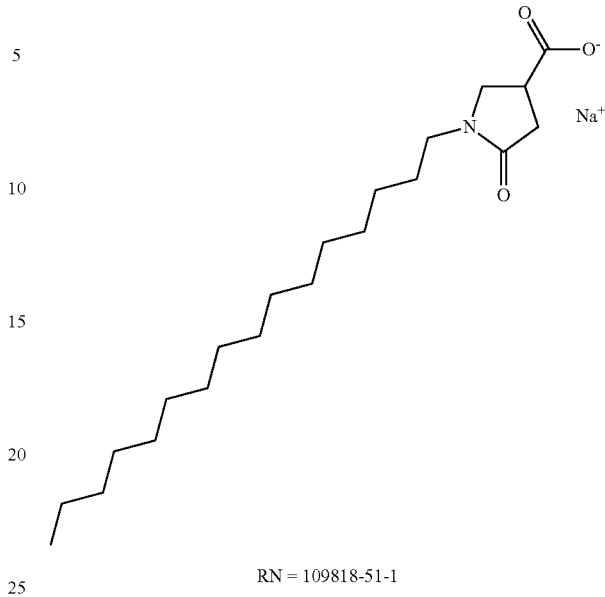

RN = 109818-51-1

(bw)

(bx)

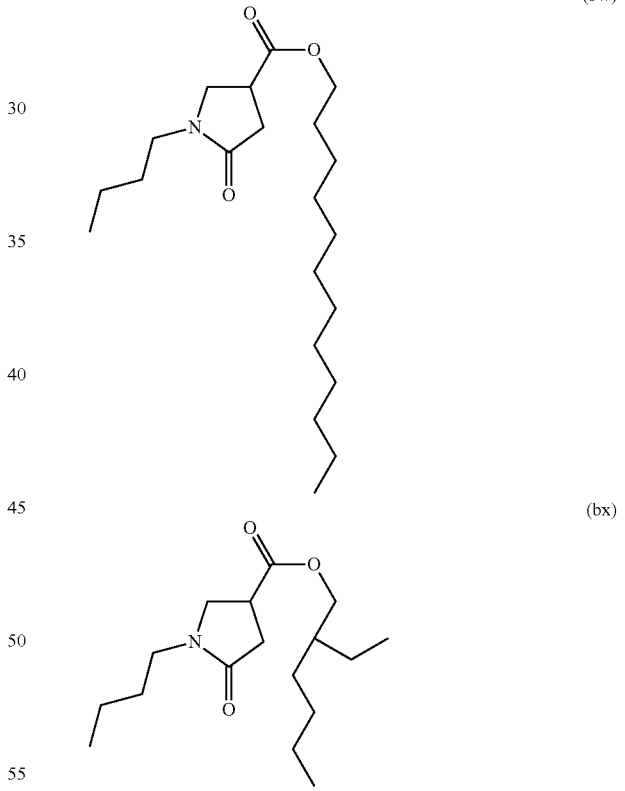

The counterions indicated can be replaced by any organic or inorganic, cosmetically acceptable cationic counterion, preferably chosen from inorganic cations of alkali metals or alkaline-earth metals, such as Na, Mg, K and Ca, and organic cations such as ammonium $NR_4^+$, with R, which may be identical or different, representing H or a $C_1$-$C_6$ (hydroxy)alkyl.

The compounds which are even more preferred are the compounds of formulae (l), (n), (o), (ac), (am), (at), (au), (av), (ba), (bg), (bl), (bm), (bp), (br), (bw) and (bx).

The compounds of formula (I) can be obtained according to the syntheses described in the following articles: J. Org. Chem., 26, pages 1519-24 (1961); Tetrahedron Asymmetric, 12 (23), pages 3241-9 (2001); J. Industrial & Engineering Chem., 47, pages 1572-8 (1955); J. Am. Chem. Soc., 60, pages 402-6 (1938); and in patents EP0069512, U.S. Pat. Nos. 2,811,496, 2,826,588, 3,136,620, FR2290199 and FR2696744.

The compounds of formula (I) are preferably present, alone or as a mixture, in the cosmetic compositions according to the invention in an amount of from 0.5% to 40% by weight Hydrophilic thickeners that may be mentioned include carboxyvinyl polymers such as the Carbopol products (carbomers) and the Pemulen products (acrylate/C10-C30-alkylacrylate copolymer); Caprylic/Capric Triglyceride and Sodium Acrylates Copolymer (Luvigel EM-BASF); polyacrylamides, for instance the crosslinked copolymers sold under the names Sepigel 305 (CTFA name: polyacrylamide/ $C_{13-14}$ isoparaffin/Laureth 7) or Simulgel 600 (CTFA name: acrylamide/sodium acryloyldimethyl taurate copolymer/isohexadecane/polysorbate 80) by the company SEPPIC; 2-acrylamido-2-methylpropanesulphonic acid polymers and copolymers, optionally crosslinked and/or neutralized, for instance poly(2-acrylamido-2-methylpropanesulphonic acid) sold by the company Clariant under the trade name Hostacerin AMPS (CTFA name: ammonium polyacryloyl dimethyl taurate or Simulgel 800 sold by the company SEPPIC (CTFA name: sodium polyacryolyl dimethyl taurate/polysorbate 80/sorbitan oleate); copolymers of 2-acrylamido-2-methylpropane sulphonic acid and of hydroxyethyl acrylate, for instance Simulgel NS and Sepinov EMT 10 sold by the company SEPPIC; cellulose derivatives such as hydroxyethyl cellulose; polysaccharides and especially gums such as xanthan gum; water-soluble or water-dispersible silicone derivatives, for instance acrylic silicones, polyether silicones and cationic silicones, and mixtures thereof.

Lipophilic thickeners that may be mentioned include synthetic polymers, such as the poly($C_{10}$-$C_{30}$ alkyl acrylates) sold under the names Intelimer IPA 13-1 and Intelimer IPA 13-6 by the company Landec, or modified clays, such as hectorite and its derivatives, for instance the products sold under the name Bentone.

Of course, a person skilled in the art will take care to select the optional additional compound(s) mentioned above and/or the amounts thereof such that the advantageous properties intrinsically associated with the compositions in accordance with the invention are not, or are not substantially, adversely affected by the envisaged addition(s).

The compositions according to the invention may be prepared according to the techniques that are well known to those skilled in the art. They may in particular be in the form of a simple or complex emulsion (O/W, W/O, O/W/O or W/O/W) such as a cream, a milk or a cream-gel; in the form of an aqueous gel; in the form of a lotion; in the form of anhydrous oil; They may optionally be packaged as an aerosol and may be in the form of a mousse or a spray.

The compositions according to the invention are preferably in the form of an oil-in-water or water-in-oil emulsion.

The emulsification processes that may be used are of the paddle or impeller, rotor-stator or HHP type.

It is also possible, via HHP (between 50 and 800 bar), to obtain stable dispersions with droplet sizes that may be as low as 100 nm.

The emulsions generally contain at least one emulsifier chosen from amphoteric, anionic, cationic and nonionic emulsifiers, used alone or as a mixture. The emulsifiers are appropriately chosen according to the emulsion to be obtained (W/O or O/W).

As emulsifying surfactants that may be used for the preparation of the W/O emulsions, examples that may be mentioned include sorbitan, glycerol or sugar alkyl esters or ethers; silicone surfactants, for instance dimethicone copolyols, such as the mixture of cyclomethicone and of dimethicone copolyol, sold under the name DC 5225 C by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R by the company Evonik, and the mixture of cetyldimethicone copolyol, of polyglyceryl isostearate (4 mol) and of hexyl laurate, sold under the name Abil WE 09 by the company Evonik. One or more co-emulsifiers may also be added thereto, which may be chosen advantageously from the group comprising polyol alkyl esters.

Polyol alkyl esters that may especially be mentioned include polyethylene glycol esters, for instance PEG-30 dipolyhydroxystearate, such as the product sold under the name Arlacel P135 by the company Croda.

Glycerol and/or sorbitan esters that may especially be mentioned include, for example, polyglyceryl isostearate, such as the product sold under the name Isolan GI 34 by the company Evonik, sorbitan isostearate, such as the product sold under the name Arlacel 987 by the company Croda, sorbitan glyceryl isostearate, such as the product sold under the name Arlacel 986 by the company Croda, and mixtures thereof.

Emulsifying polyoxyalkylenated silicone elastomers may especially be also mentioned as those disclosed in the documents U.S. Pat. Nos. 5,236,986, 5,412,004, 5,837,793, 5,811,487. Those silicone elastomers are preferably formulated under the form of a gel in a hydrocarbonated and/or a silicone oil. In those gels, the polyoxyalkylenated silicone elastomer is often under the form of spherical particles.

As example of polyoxyethylenated silicone elastomer, may be mentioned those sold by the company Shin Etsu, with the denominations:

KSG-21 (at 27% in active material) INCI name: Dimethicone/PEG-10 Dimethicone vinyl dimethicone crosspolymer), KSG-20 (at 95% % in active material) INCI name: PEG-10 Dimethicone Crosspolymer), KSG-30, (at 100% % in active material) INCI name: Lauryl PEG-15 Dimethicone vinyl dimethicone crosspolymer), KSG-31 (at 25% % in active material) INCI name: Lauryl PEG-15 Dimethicone vinyl dimethicone crosspolymer), KSG-32 or KSG-42 or KSG-320 ou KSG-30 (at 25% % in active material) INCI name: Lauryl PEG-15 Dimethicone vinyl dimethicone crosspolymer), KSG-33 (at 20% in active material), KSG-210 (at 25% % in active material) INCI name: Dimethicone/PEG-10/15 crosspolymer), KSG-310: lauryl modified polydimethylsiloxane polyoxyéthylenated in mineral oil,

KSG-330,

KSG-340,

X-226146 (at 32% % in active material) INCI name: Dimethicone/PEG-10 Dimethicone vinyl dimethicone crosspolymer), or those sold by the company Dow Corning under the commercial names:

DC9010 (at 9% % in active material) INCI name: PEG-12 dimethicone crosspolymer)

DC9011 at 11% % in active material.

Those products are generally in the form of oily gel containing the particles of silicone elastomer.

Preferably, KSG-210 is used (INCI name: Dimethicone/PEG-10/15 crosspolymer) which is at 25% in active material of silicone elastomer in a silicone oil.

Amongst water/oil emulsifiers, may be mentioned also the polyglycerolated silicone elastomers as those disclosed in the document WO-A-2004/024798.

As example of polyglycerolated silicone elastomers, may be mentioned those sold par the company Shin Etsu, with the denominations:

KSG-710, (at 25% in active material. INCI name: Dimethicone/Polyglycerin-3 Crosspolymer),
KSG-810,
KSG-820,
KSG-830,
KSG-840, For the O/W emulsions, examples of emulsifiers that may be mentioned include nonionic emulsifiers such as oxyalkylenated (more particularly polyoxyethylenated) fatty acid esters of glycerol; oxyalkylenated fatty acid esters of sorbitan; oxyalkylenated (oxyethylenated and/or oxypropylenated) fatty acid esters, for instance the mixture PEG-100 stearate/glyceryl stearate sold, for example, by the company Croda under the name Arlacel 165; oxyalkylenated (oxyethylenated and/or oxypropylenated) fatty alkyl ethers; sugar esters, for instance sucrose stearate; fatty alkyl ethers of sugars, especially alkyl polyglucosides (APG) such as decylglucoside and laurylglucoside sold, for example, by the company Cognis under the respective names Plantaren 2000 and Plantaren 1200, cetostearyl glucoside optionally as a mixture with cetostearyl alcohol, sold, for example, under the name Montanov 68 by the company SEPPIC, under the name Tegocare CG90 by the company Evonik and under the name Emulgade KE3302 by the company Cognis, and also arachidyl glucoside, for example in the form of a mixture of arachidyl alcohol, behenyl alcohol and arachidyl glucoside, sold under the name Montanov 202 by the company SEPPIC. According to a specific embodiment of the invention, the mixture of the alkyl polyglucoside as defined above with the corresponding fatty alcohol can be in the form of a self-emulsifying composition, for example as disclosed in the document WO-A-92/06778; the hydrophobically modified inulines as Inuline Lauryl Carbamate as the product sold under the denomination INUTEC SP1 by the Company Beneo-ORAFTI.

According to a specific embodiment of the invention, the composition may also contain at least an emulsifier chosen among dimers surfactants named <<gemini surfactants>> and comprising two surfactant moieties identical or different, and constituted by an hydrophilic head group and a lipophilic linked to each others through the head groups, thanks to a spacer. Such surfactants are described in the patents DE19943681, DE19943668, DE 42 27 391 et DE 196 08 117; JP-A-11-60437; JP-A-8-311003; EP 0 697 244; EP0 697 245; EP0708 079; DE19622612 and JP-A 10-17593; WO 03024412, US5863 886; WO96/25388; WO96/14926; WO 96/16930, WO 96/25384WO9740124; WO9731890; DE19750246; DE 19750245; DE 19631225; DE 19647060. In order to have a more detailed description of the chemical structures and physico-chemical properties, one can refer to the following publications: Milton J. Rosen, Gemini Surfactants, Properties of surfactant molecules with two hydrophilic groups and two hydrophobic groups, Cosmetics & Toiletries magazine, vol. 113, December 1998, pages 49-55, Milton J. Rosen, Recent Developments in Gemini Surfactants, Allured's Cosmetics & Toiletries magazine, July 2001, vol 116, no. 7, pages 67-70.

Among the dimers surfactant described above, the preferred compounds of the invention are anionic surfactants characterized by the following formula (I)

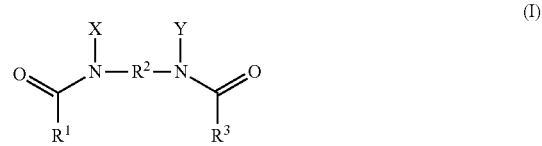

where
$R^1$ and $R^3$ represent a $C_8$-$C_{16}$ linear alkyl group,
$R^2$ represents a $C_2$-$C_8$ alkylene group,
X and Y represent an $(C_2H_4O)x$-RF with x=10-15, and RF=—$SO_3M$ group where M represent an alkaline atom.

A preferred gemini surfactant is an anionic compound Sodium Dicocoyl ethylene diamine PEG-15 Sulfate (nom INCI) with formula:

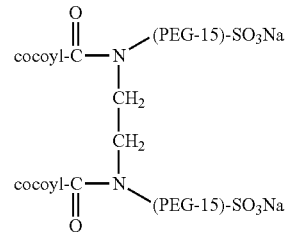

One can use for example this gemini surfactant in the commercialized mixtures sold by Sasol company under the name CERALUTION®:

Ceralution® H: Behenyl Alcohol, Glyceryl Stearate, Glyceryl Stearate Citrate et Sodium Dicocoyl ethylenediamine PEG-15 Sulfate.

Ceralution® F: Sodium Lauroyl Lactylate et Sodium Dicocoyl ethylenediamine PEG-15 Sulfate.

Ceralution® C: Aqua, Capric/Caprylic triglyceride, Glycerine, Ceteareth-25, Sodium Dicocoyl ethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI denominations).

The preferred gemini surfactant is the mixture of Behenyl Alcohol, Glyceryl Stearate, Glyceryl Stearate Citrate and Sodium Dicocoyl ethylenediamine PEG-15 Sulfate (Ceralution® H).

Among other emulsifiers, may be used isophthalic acid polymers or sulfo isophthalic acid polymers, and specifically copolymers of phthalate/sulfo isophthalate/glycol as for example Diethylene Glycol/Phthalate/Isophthalate/1,4-cyclohexane-dimethanol copolymer (INCI name: Polyester-5sol under the name <<Eastman AQ polymer>> (AQ35S, AQ38S, AQ55S, AQ48 Ultra) by the company Eastman Chemical.

Among other emulsifiers, amphiphilic copolymers of 2-acrylamido 2-methylpropane sulfonic acid as those described in the patent EP1069142, can be used. The preferred amphiphilic AMPS copolymers are AMMONIUM ACRYLOYLDIMETHYLTAURATE/STEARETH-25 METHACRYLATE CROSSPOLYMER sold under the name Aristoflex HMS by the Company Clariant, AMMONIUM ACRYLOYLDIMETHYLTAURATE/ STEARETH-8 METHACRYLATE COPOLYMER sold under the name Aristoflex SNC by the company Clariant.

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions of the invention may also contain at least one crosslinked non-emulsifying elastomer organo polysiloxane.

The term «non-emulsifying elastomer organo polysiloxane» means an emulsifying elastomer organo polysiloxane which does not contain any hydrophilic chain as polyoxyalkylenated or polyglycerolated units.

Preferably, the non-emulsifying elastomer organo polysiloxane is obtained by addition reaction (a) of diorgano polysiloxane containing at least two hydrogen atoms each linked to a silicium atom and (b) of diorgano polysiloxane having at least two insaturated ethylenic groups linked to the silicium atom, in particular in presence (c) of a platinium catalyst as disclosed in the application EP-A-295886.

According to particular form of the invention, the non-emulsifying elastomer organopolysiloxane is under the form of powder.

As examples of non-emulsifying elastomer organopolysiloxanes under the form of powder, may be used those having the INCI name: DIMETHICONE/VINYL DIMETHICONE CROSSPOLYMER as the commercial products sold under the names "DOW CORNING 9505 COSMETIC POWDER", "DOW CORNING 9506 COSMETIC POWDER" by the company DOW CORNING.

According a preferred embodiment of the invention, the non-emulsifying elastomer organopolysiloxane is mixed with at least one volatile or non-volatile hydrocarbonated and/or volatile or non-volatile silicone oil for forming a gel.

As examples of mixtures of oil/non-emulsifying elastomer organopolysiloxane, may be used those having the following INCI names:
DIMETHICONE AND DIMETHICONE/VINYL DIMETHICONECROSSPOLYMER as the commercial products sold under the name «KSG6», «KSG16» by the company SHIN ETSU,
  CYCLOPENTASILOXANE AND DIMETHICONE/VINYL DIMETHICONE CROSSPOLYMER as the commercial products sold under the name "KSG-15", "KSG 24" by the company SHIN ETSU; «Dow Corning 9040 Silicone Elastomer Blend» by the company DOW CORNING;
  DIMETHICONE AND DIMETHICONE CROSSPOLYMER as the commercial products sold under the name <<Dow Corning 9041 Silicone Elastomer Blend>> by the company DOW CORNING;
  MINERAL OIL AND Vinyl Dimethicone/Lauryl Dimethicone Crosspolymer as "KSG 41" by the company SHIN ETSU
  ISODODECANE AND Vinyl Dimethicone/Lauryl Dimethicone Crosspolymer as "KSG 42" sold by the company SHIN ETSU
  TRIETHYLHEXANOIN AND VINYL DIMETHICONE/LAURYL DIMETHICONE CROSSPOLYMER as <<KSG 43>> sold by the company SHIN ETSU;
  SQUALANE AND VINYL DIMETHICONE/LAURYL DIMETHICONE CROSSPOLYMER as "KSG 44" sold by the company SHIN ETSU.

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another object of the present invention consists of the use of the compositions according to the invention as defined above for the manufacture of cosmetic products for treating the skin, the lips, the nails, the hair, the eyelashes, the eyebrows and/or the scalp, especially care products, antisun protection products and makeup products.

The cosmetic compositions according to the invention may be used, for example, as makeup products.

The cosmetic compositions according to the invention may be used, for example, as care products and/or antisun protection products for the face and/or the body, of liquid to semi-liquid consistency, such as milks, more or less rich creams, cream-gels and pastes. They may optionally be packaged as an aerosol and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and also aerosol pumps using compressed air as propellant. These devices are described in patents U.S. Pat. Nos. 4,077,441 and 4,850,517.

The compositions conditioned in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The compositions according to the invention may additionally, further, comprise additional cosmetic and dermatological active agents.

It will be possible especially to choose the additional active agents from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, tensioning agents, lipid restructuring agents, slimming agents, agents for promoting the cutaneous microcirculation, calmatives and/or anti-irritants, sebo-regulating or anti-seborrhoeic agents, astringents, cicatrizing agents, anti-inflammatory agents, anti-acne agents and agents which promote natural colouring of the skin.

A person skilled in the art will select the said active agent or agents as a function of the desired effect on the skin, hair, eyelashes, eyebrows or nails.

For caring for and/or making up skin which has aged, he or she will preferably select at least one active agent chosen from moisturizers, desquamating agents, agents for improving the barrier function, depigmenting agents, antioxidants, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, lipid restructuring agents, agents promoting the cutaneous microcirculation for the area around the eyes and agents which promote the natural colouring of the skin.

For caring for and/or making up greasy skin, the person skilled in the art will preferably select at least one active agent chosen from desquamating agents, sebo-regulating or antiseborrhoeic agents and astringents. According to a preferred embodiment, the cosmetic and/or dermatological active is a Depigmenting agent.

As depigmenting agents that can be used in accordance with the present invention, mention may in particular be made of vitamin C and derivatives thereof, and in particular vitamin CG, vitamin CP and 3-O ethyl vitamin C; arbutin and derivatives thereof, such as those described in applications EP895779 and EP524109, for instance alpha- and beta-arbutin; hydroquinone; aminophenol derivatives such as those described in applications WO 99/10318 and WO 99/32077, and in particular N-cholesteryl oxycarbonyl-para-aminophenol and N-ethyloxycarbonyl-para-aminophenol; iminophenol derivatives such as those described in application WO 99/22707; L-2-oxothiazolidine-4-carboxylic acid or procysteine and also salts or esters thereof; ferulic acid; lucinol and derivatives thereof; kojic acid; resorcinol and esters thereof; tranexamic acid and esters thereof; gentisic acid, homogentisate, or methyl gentisate or homogentisate; dioic acid; calcium D-pantethein sulphonate; lipoic acid; ellagic acid; vitamin B3; linoleic acid and derivatives thereof; ceramides and homologues thereof; derivatives of plants, for instance camomile, bearberry, the aloe family (vera, ferox, bardensis), mulberry or skullcap; a kiwi fruit (*Actinidia chinensis*) juice sold by Gattefosse; an extract of *Paeonia suffructicosa* root, such as the product sold by the company Ichimaru Pharcos under the name Botanpi Liquid B®, an extract of brown sugar (*Saccharum officinarum*), such as the extract of molasses sold by the company Taiyo Kagaku under the name Molasses Liquid, without this list being exhaustive. Mention may also be made of biphenyl compounds such as magnolol, honokiol, magnolignan, etc, We can also mention hydroxylated diphenylmethane derivatives as those described in application WO 2004/105736 and particularly the compound of structure:

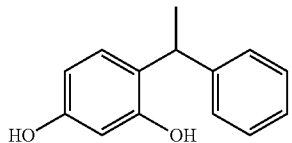 [SMILES: CC(c1ccccc1)c1ccc(O)cc1O]

known as 4-(1-phenylethyl)-1,3-benzenediol or 4-(1-phenylethyl)-1,3-dihydroxybenzene or otherwise known as phenylethyl resorcinol or phenylethylbenzenediol or styryl resorcinol. This compound has a CAS number 85-27-8. Such a compound is sold under the name Symwhite 377® by the company Symrise.

Mention may be made especially of:

a self-tanning agent, i.e. an agent which, when applied to the skin, especially to the face, can produce a tan effect that is more or less similar in appearance to that which may result from prolonged exposure to the sun (natural tan) or under a UV lamp;

an additional colouring agent, i.e. any compound that has a particular affinity for the skin, which allows it to give the skin a lasting, non-covering coloration (i.e. that does not have a tendency to opacify the skin) and that is not removed either with water or using a solvent, and that withstands both rubbing and washing with a solution containing surfactants. Such a lasting coloration is thus distinguished from the superficial and transient coloration provided, for example, by a makeup pigment; and mixtures thereof.

The self-tanning agents may be chosen from
(i) the compounds interfering with the melanogenesis biological pathway to potentiate it such as for example tyrosinase substrate, MC1R agonists;
(ii) the monocarbonyl or polycarbonyl compounds, for instance isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxyacetone (DHA) and 4,4-dihydroxypyrazolin-5-one derivatives as described in patent application EP 903 342. DHA will preferably be used.

The DHA may be used in free and/or encapsulated form, for example in lipid vesicles such as liposomes, especially described in patent application WO 97/25970.

In general, the self-tanning agent is present in an amount ranging from 0.01% to 20% by weight and preferably in an amount of between 0.1% and 10% of the total weight of the composition.

Other dyes that allow modification of the colour produced by the self-tanning agent may also be used.

These dyes may be chosen from synthetic or natural direct dyes.

These dyes may be chosen, for example, from red or orange dyes of the fluoran type such as those described in patent application FR 2 840 806. Mention may be made, for example, of the following dyes:

tetrabromofluorescein or eosin known under the CTFA name: CI 45380 or Red 21;
phloxin B known under the CTFA name: CI 45410 or Red 27;
diiodofluorescein known under the CTFA name: CI 45425 or Orange 10;
dibromofluorescein known under the CTFA name: CI 45370 or Orange 5;
the sodium salt of tetrabromofluorescein known under the CTFA name: CI 45380 (Na salt) or Red 22;
the sodium salt of phloxin B known under the CTFA name: CI 45410 (Na salt) or Red 28;
the sodium salt of diiodofluorescein known under the CTFA name: CI 45425 (Na salt) or Orange 11;
erythrosine known under the CTFA name: CI 45430 or Acid Red 51;
phloxin known under the CTFA name: CI 45405 or Acid Red 98.

These dyes may also be chosen from anthraquinones, caramel, carmine, carbon black, azulene blues, methoxalene, trioxalene, guajazulene, chamuzulene, Bengal rose, cosin 10B, cyanosin and daphinin.

These dyes may also be chosen from indole derivatives, for instance the monohydroxyindoles as described in patent FR 2 651 126 (i.e.: 4-, 5-, 6- or 7-hydroxy-indole) or the dihydroxyindoles as described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

The cosmetic and/or dermatological active agents will be present in one of the compositions according to the invention in a content ranging from 0.001% to 20% by weight relative to the total weight of the composition, preferably from 0.01% to 10%, more preferably still from 0.5 to 5% and more preferably from 0.1 to 1% by weight relative to the total weight of the composition.

The following photoprotective formulations were produced; the amounts are given as weight percentages relating to the total weight of the composition.

EXAMPLES

A. Preparation Examples of Merocyanine UV Absorbers

Example A1

Preparation of the Compound (1)

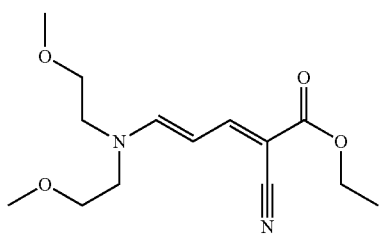

(1)

55.33 grams of bis-(2-methoxyethyl)amine are reacted with 1,1,3,3-tetramethoxypropane in acetic acid, concentrated and treated with 21.48 grams of ethyl cyanoacetate in the presence of an organic base and a solvent.

The following base/solvent combinations are used:

| Example | Base | Solvent |
|---|---|---|
| Example A1.1 | DBU (1,8-diazabicyclo[5.4.0]undec-7-ene) | dimethylformamide |
| Example A1.2 | DBN (1,5-diazabicyclo[4.3.0]non-5-ene) | dimethylacetamide |
| Example A1.3 | DBN (1,5-diazabicyclo[4.3.0]non-5-ene) | 1-methylpyrrolidone |
| Example A1.4 | DBN (1,5-diazabicyclo[4.3.0]non-5-ene) | dimethylsulfoxide |
| Example A1.5 | DBU (1,8-diazabicyclo[5.4.0]undec-7-ene) | dimethylformamide |
| Example A1.6 | sodium methylate | dimethylacetamide |
| Example A1.7 | sodium methylate | isopropanol |
| Example A1.8 | potassium t-butoxide | t-butanol |

The reaction temperature is between 0° C. and the boiling point of the solvent.

The reaction end point is confirmed by thin layer chromatography or high performance liquid chromatography.

After the reaction, the product (101) is obtained from the reaction mixture through ordinary product isolation by liquid-liquid separation, column chromatography or crystallization by addition of a poor solvent to the reaction mixture.

The desired product (1) is obtained in yields of 66% (36 grams) as a dark brownish oil which crystallized as yellow crystals (Melting point: 76.9° C.)

Example A2

Preparation of the Compound of Formula of the Compound (2)

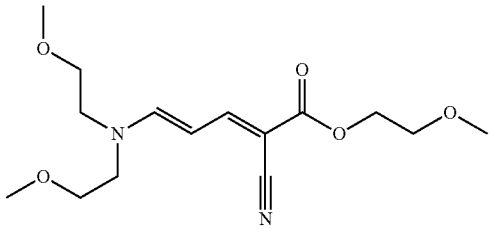

(2)

55.33 grams of bis-(2-methoxyethyl)amine are condensed with 1,1,3,3-tetramethoxypropane in acetic acid, concentrated and treated with 27.18 grams of 2-methoxyethylcyanoacetate in the presence of an organic base and a solvent.

The following base/solvent combinations are used:

| Example | Base | Solvent |
|---|---|---|
| Example A2.1 | DBU (1,8-diazabicyclo[5.4.0]undec-7-ene) | dimethylformamide |
| Example A2.2 | DBN (1,5-diazabicyclo[4.3.0]non-5-ene) | dimethylacetamide |
| Example A2.3 | DBN (1,5-diazabicyclo[4.3.0]non-5-ene) | 1-methylpyrrolidone |
| Example A2.4 | DBN (1,5-diazabicyclo[4.3.0]non-5-ene) | dimethylsulfoxide |
| Example A2.5 | DBU (1,8-diazabicyclo[5.4.0]undec-7-ene) | dimethylformamide |
| Example A2.6 | N-methylmorpholine | dimethylacetamide |
| Example A2.7 | bis-(2-methoxyethyl)amine | 1-methylpyrrolidone |
| Example A2.8 | sodium methylate | dimethylsulfoxide |

After the reaction, the product (102) is obtained from the reaction mixture through silica gel column chromatography (eluent: toluene/acetone).

The desired product (2) is obtained in yields of 75% (45.44 grams) as a yellow powder (melting point: 92.2° C.)

Example A3

Preparation of the Compound (3)

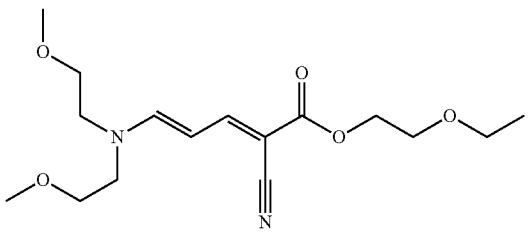

55.33 grams of bis-(2-methoxyethyl)amine are condensed with 1,1,3,3-tetramethoxypropane in acetic acid, concentrated and treated with 29.85 grams of 2-ethoxyethyl-cyanoacetate in the presence of an organic base and a solvent The following base/solvent combinations are used:

| Example | Base | Solvent |
| --- | --- | --- |
| Example A3.1 | DBU (1,8-diazabicyclo[5.4.0]undec-7-ene) | dimethylformamide |
| Example A3.2 | DBN (1,5-diazabicyclo[4.3.0]non-5-ene) | dimethylacetamide |
| Example A3.3 | DBN (1,5-diazabicyclo[4.3.0]non-5-ene) | 1-methylpyrrolidone |
| Example A3.4 | DBN (1,5-diazabicyclo[4.3.0]non-5-ene) | dimethylsulfoxide |
| Example A3.5 | DBU (1,8-diazabicyclo[5.4.0]undec-7-ene) | dimethylformamide |
| Example A3.6 | N-methylmorpholine | dimethylacetamide |
| Example A3.7 | bis-(2-methoxyethyl)amine | 1-methylpyrrolidone |
| Example A3.8 | sodium methylate | dimethylsulfoxide |

After the reaction, the product (103) is obtained from the reaction mixture through ordinary product isolation by liquid-liquid separation, column chromatography or crystallization by addition of a poor solvent to the reaction mixture.

The desired product (103) is obtained in yields of 66% (39.99 grams) as beige crystals (melting point: 58.3° C.)

Example A4

Preparation of the Compound (4)

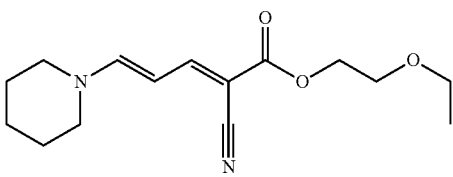

70.67 grams of piperidine are condensed with 1,1,3,3-tetramethoxypropane in acetic acid, concentrated and treated with 59.72 grams of 2-ethoxyethyl cyanoacetate cyanoacetate in the presence of an organic base and a solvent.

The following base/solvent combinations are used:

| Example | Base | Solvent |
| --- | --- | --- |
| Example A4.1 | DBU (1,8-diazabicyclo[5.4.0]undec-7-ene) | dimethylformamide |
| Example A4.2 | DBN (1,5-diazabicyclo[4.3.0]non-5-ene) | dimethylacetamide |
| Example A4.3 | DBN (1,5-diazabicyclo[4.3.0]non-5-ene) | 1-methylpyrrolidone |
| Example A4.4 | DBN (1,5-diazabicyclo[4.3.0]non-5-ene) | dimethylsulfoxide |
| Example A4.5 | DBU (1,8-diazabicyclo[5.4.0]undec-7-ene) | dimethylformamide |
| Example A4.6 | piperidine | dimethylacetamide |
| Example A4.7 | piperidine | 1-methylpyrrolidone |
| Example A4.8 | sodium methylate | dimethylsulfoxide |

After silica gel column chromatography (eluent: toluene/acetone) the pure product is obtained yielding dark yellow crystals. Melting point: 66-67° C.

Example A5a

Preparation of Compound (5)

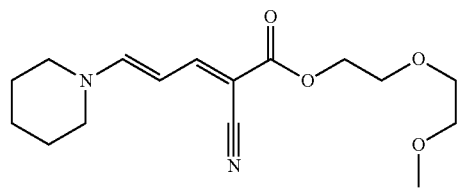

132.83 grams of piperidine are condensed with 1,1,3,3-tetramethoxypropane in acetic acid, concentrated and treated with 133.38 grams of 2-(2-methoxyethoxy)-ethyl-cyanoacetate in the presence of an organic base and a solvent.

The following base/solvent combinations are used:

| Example | Base | Solvent |
| --- | --- | --- |
| Example A5a.1 | DBU (1,8-diazabicyclo[5.4.0]undec-7-ene | dimethylformamide |
| Example A5a.2 | DBN (1,5-diazabicyclo[4.3.0]non-5-ene) | dimethylacetamide |
| Example A5a.3 | DBN (1,5-diazabicyclo[4.3.0]non-5-ene) | 1-methylpyrrolidone |
| Example A5a.4 | DBN (1,5-diazabicyclo[4.3.0]non-5-ene) | dimethylsulfoxide |
| Example A5a.5 | DBU (1,8-diazabicyclo[5.4.0]undec-7-ene) | dimethylformamide |
| Example A5a.6 | piperidine | dimethylacetamide |
| Example A5a.7 | piperidine | 1-methylpyrrolidone |
| Example A5a.8 | sodium methylate | dimethylsulfoxide |

The desired product (5) is obtained in yields of 38% (82.4 grams) as an dark oil.

After column chromatography over silica gel and toluene/acetone (9:1) as eluent the product (105) crystallizes from water as orange crystals. Melting point: 43.5-45° C.

Example A5b

Preparation of the Compound (5)

By using 5 grams of 3-(1-piperidinyl)-2-propenal and 7.39 grams of 2-(2-methoxyethoxy)ethyl-2-cyano acetic acid ester in the presence of a base and optionally a solvent the desired product is obtained in yields of 32% (3.5 grams) as an dark oil.

The following base/solvent combinations are used:

| Example | Base | Solvent |
|---|---|---|
| Example A5b.1 | piperidine | no solvent |
| Example A5b.2 | N-methylmorpholine | dimethylacetamide |
| Example A5b.3 | piperidine | 1-methylpyrrolidone |
| Example A5b.4 | piperidine | dimethylsulfoxide |

Example A6

Preparation of the Compound (6)

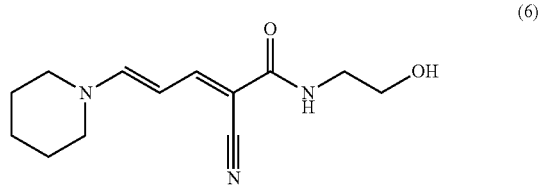 [SMILES: N#C/C(=C\C=C\N1CCCCC1)C(=O)NCCO]

(6)

2.89 grams of piperidine are condensed with 1,1,3,3-tetramethoxypropane in acetic acid, concentrated and treated with 1.22 grams of 2-cyano-N-(2-hydroxyethyl)acetamide in the presence of an organic base and a solvent.

The following base/solvent combinations are used:

| Example | Base | Solvent |
|---|---|---|
| Example A6.1 | DBU (1,8-diazabicyclo[5.4.0]undec-7-ene) | dimethylformamide |
| Example A6.2 | DBN (1,5-diazabicyclo[4.3.0]non-5-ene) | dimethylacetamide |
| Example A6.3 | DBN (1,5-diazabicyclo[4.3.0]non-5-ene) | 1-methylpyrrolidone |
| Example A6.4 | ethanolamine | dimethylsulfoxide |
| Example A6.5 | ethanolamine | dimethylformamide |
| Example A6.6 | piperidine | dimethylacetamide |
| Example A6.7 | piperidine | 1-methylpyrrolidone |
| Example A6.8 | sodium methylate | dimethylsulfoxide |

The reaction end point is confirmed by thin layer chromatography or high performance liquid chromatography.

After the reaction, the product (6) is obtained from the reaction mixture through ordinary product isolation by liquid-liquid separation, column chromatography or crystallization by addition of a poor solvent to the reaction mixture.

The desired product (6) is obtained as a brownish oil which crystallizes in form of yellow crystals (0.24 g, 10%).

Melting point: 139.4-141.0° C.

Example A7

Preparation of Compound (20)

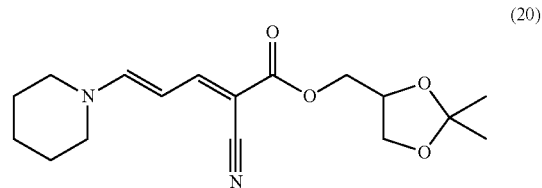 [SMILES: CC1(C)OCC(COC(=O)/C(C#N)=C/C=C/N2CCCCC2)O1]

(20)

27.84 grams of piperidine are condensed with 1,1,3,3-tetramethoxypropane in acetic acid, concentrated and treated with 56.77 grams of (2,2-dimethyl-1,3-dioxolan-4-yl) methyl cyanoacetate in the presence of an organic base and a solvent.

The following base/solvent combinations are used:

| Example | Base | Solvent |
|---|---|---|
| Example A7.1 | DBU (1,8-diazabicyclo[5.4.0]undec-7-ene) | dimethylformamide |
| Example A7.2 | DBN (1,5-diazabicyclo[4.3.0]non-5-ene) | dimethylacetamide |
| Example A7.3 | DBN (1,5-diazabicyclo[4.3.0]non-5-ene) | 1-methylpyrrolidone |
| Example A7.4 | DBN (1,5-diazabicyclo[4.3.0]non-5-ene) | dimethylsulfoxide |
| Example A7.5 | DBU (1,8-diazabicyclo[5.4.0]undec-7-ene) | dimethylformamide |
| Example A7.6 | piperidine | dimethylacetamide |
| Example A7.7 | piperidine | 1-methylpyrrolidone |
| Example A7.8 | piperidine | dimethylsulfoxide |

74.74 grams of the compound (20) are obtained yielding yellow crystals.

Example A8

Preparation of Compound (7)

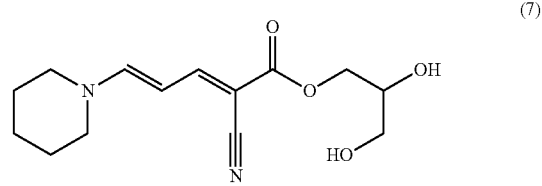 [SMILES: N#C/C(=C\C=C\N1CCCCC1)C(=O)OCC(O)CO]

(7)

70 ml of hydro chloride acid (1 N) are added to a solution of 74.74 grams of merocyanine compound (20) in 350 ml of ethanol. The reaction mixture is stirred for hours at 40° C. After adding water the product is extracted several times with ethyl acetate. The combined organic phases are dried with sodium sulphate, filtrated and concentrated under vacuum yielding the crude product as a brown oil.

After crystallization 34.44 grams of the product is yielded as a yellow powder.

Melting point: 101° C.

Example A9

Preparation of the Compound of (8)

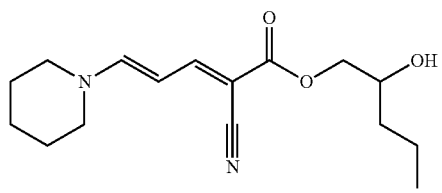
(8)

236.72 grams of piperidine are condensed with 1,1,3,3-tetramethoxypropane in acetic acid, concentrated and treated with 217.24 grams of 1-(2-hydroxy)pentyl cyanoacetate in the presence of an organic base and a solvent.

The following base/solvent combinations are used:

| Example | Base | Solvent |
|---|---|---|
| Example A9.1 | DBU (1,8-diazabicyclo[5.4.0]undec-7-ene) | dimethylformamide |
| Example A9.2 | DBU (1,8-diazabicyclo[5.4.0]undec-7-ene) | dimethylacetamide |
| Example A9.3 | piperidine | 1-methylpyrrolidone |
| Example A9.4 | piperidine | dimethylsulfoxide |
| Example A9.5 | DBU (1,8-diazabicyclo[5.4.0]undec-7-ene) | dimethylformamide |
| Example A9.6 | DBU (1,8-diazabicyclo[5.4.0]undec-7-ene) | dimethylacetamide |
| Example A9.7 | DBU (1,8-diazabicyclo[5.4.0]undec-7-ene) | 1-methylpyrrolidone |
| Example A9.8 | DBU (1,8-diazabicyclo[5.4.0]undec-7-ene) | dimethylsulfoxide |

500 grams of the crude product (109) are obtained yielding a dark brown oil.

After column chromatography (silica gel, eluent: toluene/ethyl acetate) and crystallization 53.09 grams (23%) of the desired product are obtained yielding yellow crystals.

Melting point: 130° C.

Example A10

Preparation of Compound (21)

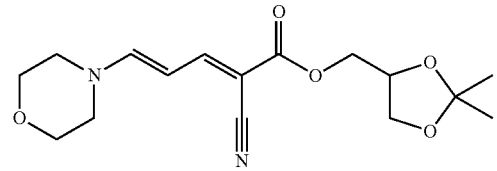
(21)

1.81 grams of morpholine are treated with 1,1,3,3-tetramethoxypropane in acetic acid, concentrated and treated with 1.89 grams of (2,2-dimethyl-1,3-dioxolan-4-yl)methyl cyanoacetate in the presence of an organic base and a solvent.

The following base/solvent combinations are used:

| Example | Base | Solvent |
|---|---|---|
| Example A10.1 | DBU (1,8-diazabicyclo[5.4.0]undec-7-ene) | dimethylformamide |
| Example A10.2 | DBU (1,8-diazabicyclo[5.4.0]undec-7-ene) | dimethylacetamide |
| Example A10.3 | DBN (1,5-diazabicyclo[4.3.0]non-5-ene) | 1-methylpyrrolidone |
| Example A10.4 | morpholine | dimethylsulfoxide |
| Example A10.5 | morpholine | dimethylformamide |
| Example A10.6 | morpholine | dimethylacetamide |
| Example A10.7 | sodium methylate | isopropanol |
| Example A10.8 | sodium methylate | dimethylsulfoxide |

2.99 grams of the crude product (110) are obtained yielding a dark brown oil.

After column chromatography (silica gel, eluent: toluene/acetone) and crystallization 1.17 grams (50%) of the compound (110) are obtained yielding yellowish crystals.

Example A11

Preparation of the Compound (9)

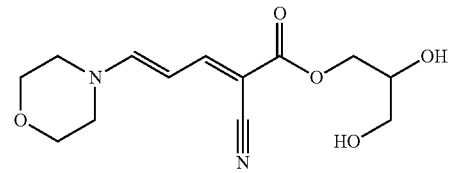
(9)

1 ml of hydro chloride acid (1 N) are added to a solution of 1.17 grams of merocyanine compound (21) in 5 ml of ethanol. The reaction mixture is stirred for 16 hours at room temperature.

The product is filtered off and washed with small amounts of ethanol and water. After drying under vacuum 0.36 grams of the product is yielded as a yellowish powder.

Melting point: 144.5-146.0° C.

Example A12

Preparation of the Compound (10)

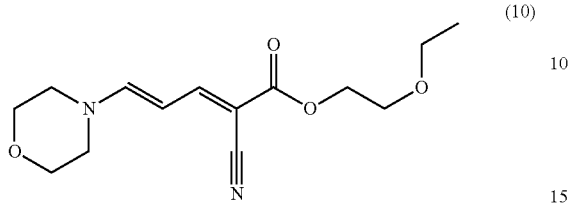

83.40 grams of morpholine are condensed with 1,1,3,3-tetramethoxypropane in acetic acid and treated with 47.15 grams of 2-ethoxyethyl cyanoacetate in the presence of the organic base and a solvent.

The following base/solvent combinations are used:

| Example | Base | Solvent |
|---|---|---|
| Example A12.1 | DBU (1,8-diazabicyclo[5.4.0]undec-7-ene) | dimethylformamide |
| Example A12.2 | DBN (1,5-diazabicyclo[4.3.0]non-5-ene) | dimethylacetamide |
| Example A12.3 | DBN (1,5-diazabicyclo[4.3.0]non-5-ene) | 1-methylpyrrolidone |
| Example A12.4 | DBN (1,5-diazabicyclo[4.3.0]non-5-ene) | dimethylsulfoxide |
| Example A12.5 | DBU (1,8-diazabicyclo[5.4.0]undec-7-ene) | dimethylformamide |
| Example A12.6 | morpholine | dimethylacetamide |
| Example A12.7 | morpholine | 1-methylpyrrolidone |
| Example A12.8 | sodium methylate | dimethylsulfoxide |

32.58 grams of the compound (10) are obtained yielding yellow crystals.

Melting point: 81.5° C.

Example A13

Preparation of the Compound (12)

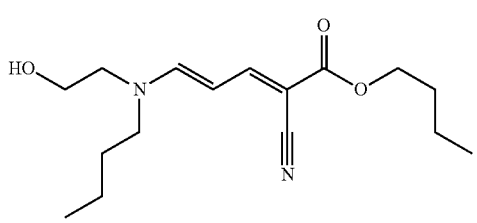

The merocyanine compound (12) is synthesized according to a method described on pages 367-371 in Synthetic Communications Vol. 33, No. 3, 2003.

By using 113.00 grams of ethyl-2-hydroxyethylaminoacrolein and 102.47 grams of n-butyl cyanoacetate 123.46 grams of the crude product are obtained yielding a brown oil.

After crystallization 23.29 g of the product is obtained yielding yellowish crystals.

Melting point: 78.0° C.

Example A14

Preparation of the Compound (13)

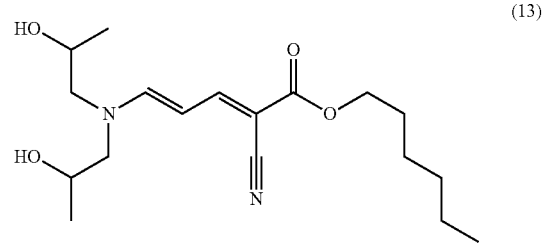 [SMILES: CCCCCCOC(=O)/C(C#N)=C/C=C/N(CC(C)O)CC(C)O]

The merocyanine compound (13) is synthesized according to the synthesis of merocyanine 12 yielding the desired product as a brownish oil. 1H-NMR (CDCl3):

δ=7.73 (1H, d), 7.24 (1H, d), 5.5 (1H, t), 4.07-4.33 (5H, m), 3.44-3.55 (2H, m), 3.16-3.26 (2H, m), 1.67 (2H, m), 1.22-1.45 (12H, m), 0.9 (3H, m).

Example A15

Preparation of the Compound (14)

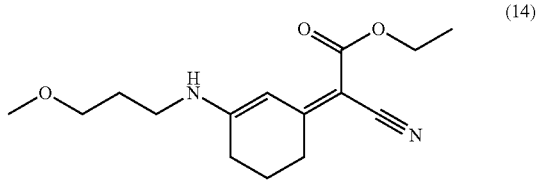 [SMILES: CCOC(=O)/C(C#N)=C1\C=C(NCCCOC)CCC1]

122.23 grams of 3-[(3-methoxypropyl)amino]-2-cyclohexen-1-one are alkylated with dimethylsulfate or alternatively with diethylsulfate and treated with 75.45 grams of ethyl cyanoacetate in approximately equimolar proportions in the presence of a base and optionally a solvent.

The following base/solvent combinations are used:

| Example | Base | Solvent |
|---|---|---|
| Example A15.1 | DBU (1,8-diazabicyclo[5.4.0]undec-7-ene) | dimethylacetamide |
| Example A15.2 | triethylamine | isopropanol |
| Example A15.3 | 3-methoxypropylamine | isopropanol |
| Example A15.4 | 3-methoxypropylamine | tert-amylalcohol |
| Example A15.5 | 3-methoxypropylamine | toluene |
| Example A15.6 | 3-methoxypropylamine | dimethylformamide |

-continued

| Example | Base | Solvent |
| --- | --- | --- |
| Example A15.7 | 3-methoxypropylamine | no solvent |
| Example A15.8 | N-morpholine | isopropanol |

Completion of the alkylation reaction can be monitored for example by TLC, GC or HPLC methods.

162.30 grams of the product (115) are obtained yielding a brown oil.

After crystallization the product is obtained yielding yellowish crystals.

Melting point: 92.7° C.

Example A16

Preparation of the Compound (15)

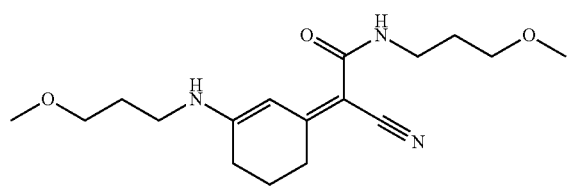
(15)

101.00 grams of 3-[(3-methoxypropyl)amino]-2-cyclohexen-1-one are alkylated with dimethylsulfate or alternative with diethylsulfate and treated with 86.00 grams of 2-cyano-N-(3-methoxy-propyl)-acetamide in approximately equimolar proportions in the presence of a base and optionally a solvent.

The following base/solvent combinations are used:

| Example | Base | Solvent |
| --- | --- | --- |
| Example A16.1 | DBU (1,8-diazabicyclo[5.4.0]undec-7-ene) | dimethylacetamide |
| Example A16.2 | triethylamine | isopropanol |
| Example A16.3 | 3-methoxypropylamine | isopropanol |
| Example A16.4 | 3-methoxypropylamine | tert-amylalcohol |
| Example A16.5 | 3-methoxypropylamine | toluene |
| Example A16.6 | 3-methoxypropylamine | dimethylformamide |
| Example A16.7 | 3-methoxypropylamine | no solvent |

The crude product (15) is obtained yielding a dark brown oil.

After silica gel column chromatography (eluent:

toluene/methanol 99:1) 81.8 grams of the product are obtained yielding yellowish crystals.

Melting point: 84.7-85.3° C.

Example A17

Preparation of the Compound (16)

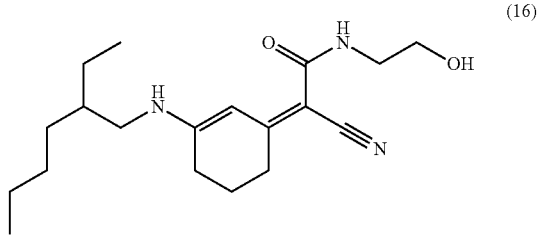 [SMILES: CCCCC(CC)CNC1=C/C(=C(/C#N)C(=O)NCCO)CCC1]
(16)

111.0 grams of 3-[(2-ethylhexyl)amino]-2-cyclohexen-1-one are alkylated with dimethylsulfate or alternatively with diethylsulfate and are then treated with 64.10 grams of 2-cyano-N-(2-hydroxy-ethyl)-acetamide in the presence of a base and optionally a solvent.

The following base/solvent combinations are used:

| Example. | Base | Solvent |
| --- | --- | --- |
| Example A17.1 | DBU (1,8-diazabicyclo[5.4.0]undec-7-ene) | dimethylacetamide |
| Example A17.2 | triethylamine | isopropanol |
| Example A17.3 | ethanolamine | isopropanol |
| Example A17.4 | 2-ethylhexylamine | tert-amylalcohol |
| Example A17.5 | ethanolamine | toluene |
| Example A17.6 | ethanolamine | dimethylformamide |
| Example A17.7 | ethanolamine | no solvent |

The reaction temperature is between 60 to 120° C.

The crude product is obtained yielding brownish crystals.

After recrystallization 97 grams of the product were obtained yielding yellowish crystals. Melting point: 117-119° C.

Example A18

Preparation of the Compound (17)

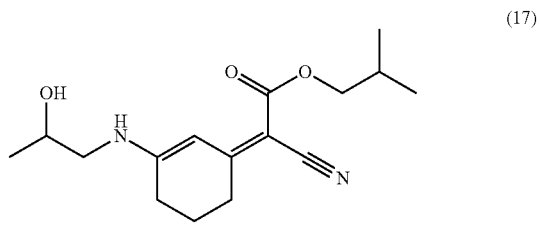 [SMILES: CC(C)COC(=O)/C(C#N)=C1\C=C(NCC(C)O)CCC1]
(17)

100.56 grams of 3-[(2-hydroxypropyl)amino]-2-cyclohexen-1-one are alkylated with dimethylsulfate or alternatively with diethylsulfate and treated with 84.70 grams of isobutyl cyanoacetate in the presence of a base and optionally a solvent.

The following base/solvent combinations are used:

| Example | Base | Solvent |
|---|---|---|
| Example A18.1 | DBU (1,8-diazabicyclo[5.4.0]undec-7-ene) | dimethylacetamide |
| Example A18.2 | triethylamine | isopropanol |
| Example A18.3 | 1-amino-2-propanol | isopropanol |
| Example A18.4 | N-methylmorpholine | tert-amylalcohol |
| Example A18.5 | 1-amino-2-propanol | toluene |
| Example A18.6 | 1-amino-2-propanol | dimethylformamide |
| Example A18.7 | 1-amino-2-propanol | no solvent |

15.97 grams of the crude product (17) is obtained yielding a dark brown oil.

After silica gel chromatography (eluent: hexane/ethyl acetate) 45.67 grams of the product were obtained yielding yellowish crystals. Melting point: 106.7° C.

Example A19

Preparation of the Compound (27)

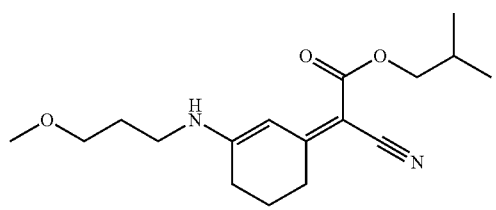

(27)

13.09 grams of 3-[(3-methoxypropyl)amino]-2-cyclohexen-1-one are alkylated with dimethylsulfate or alternatively with diethylsulfate and treated with 10.12 grams of isobutyl cyanoacetate in the presence of a base and optionally a solvent.

The following base/solvent combinations are:

| Example | Base | Solvent |
|---|---|---|
| Example A19.1 | DBU (1,8-diazabicyclo[5.4.0]undec-7-ene) | dimethylacetamide |
| Example A19.2 | triethylamine | isopropanol |
| Example A19.3 | 3-methoxypropylamine | isopropanol |
| Example A19.4 | N-methylmorpholine | tert-amylalcohol |
| Example A19.5 | 3-methoxypropylamine | toluene |
| Example A19.6 | 3-methoxypropylamine | dimethylformamide |
| Example A19.7 | 3-methoxypropylamine | no solvent |

15.97 grams of the crude product (27) are obtained yielding a dark brown oil.

After silica gel chromatography (eluent: toluene/acetone) 13.46 grams of the product were obtained yielding yellowish crystals. Melting point: 96.3° C.

Example A20

Preparation of the Compound (22)

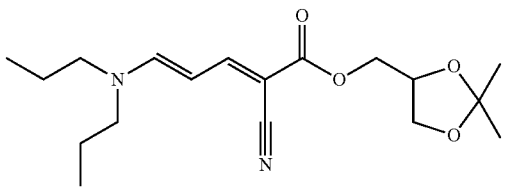

(22)

222.62 grams of dipropylamine are condensed with 1,1,3,3-tetramethoxypropane in acetic acid and treated with 200.13 grams of (2,2-dimethyl-1,3-dioxolan-4-yl)methyl cyanoacetate in the presence of an organic base and a solvent as described on page 4 in US2003/0181483A1.

The following Base/solvent combinations are used:

| Example | Base | Solvent |
|---|---|---|
| Example A20.1 | DBU (1,8-diazabicyclo[5.4.0]undec-7-ene) | dimethylformamide |
| Example A20.2 | DBN (1,5-diazabicyclo[4.3.0]non-5-ene) | dimethylacetamide |
| Example A20.3 | DBN (1,5-diazabicyclo[4.3.0]non-5-ene) | 1-methylpyrrolidone |
| Example A20.4 | DBN (1,5-diazabicyclo[4.3.0]non-5-ene) | dimethylsulfoxide |
| Example A20.5 | DBU (1,8-diazabicyclo[5.4.0]undec-7-ene) | dimethylformamide |
| Example A20.6 | dipropylamine | dimethylacetamide |
| Example A20.7 | sodium methylate | 1,2-dimethoxyethane |
| Example A20.8 | N-methylmorpholine | dimethylsulfoxide |

327 grams of the crude product (22) are obtained yielding a brown oil.

Example A21

Preparation of the Compound (23)

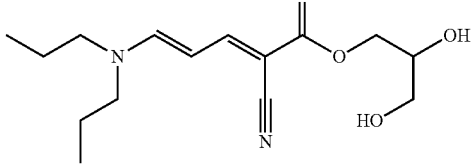

(23)

317 ml of hydro chloride acid (1 N) are added to a solution of 327 grams of crude merocyanine (22) in 990 ml of ethanol.

The reaction mixture is stirred for 16 hours at room temperature.

After removal of ethanol in vacuum the reaction mass was taken up in water and the product is extracted several times with ethyl acetate.

The collected organic phases are concentrated in vacuum.

After silica gel column chromatography (eluent: toluene/ethyl acetate) and crystallization 70 grams of the desired product are obtained yielding yellowish crystals.

Melting point: 73° C.

Example A22

Preparation of the Compound (24)

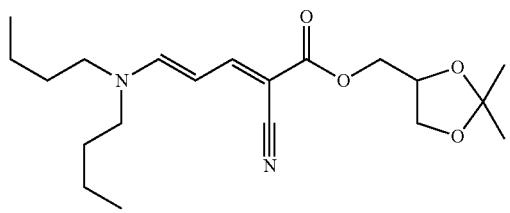
(24)

66.43 grams of dibutylamine are condensed with 1,1,3,3-tetramethoxypropane in acetic acid and treated with 46.81 grams of (2,2-dimethyl-1,3-dioxolan-4-yl)methyl cyanoacetate in the presence of an organic base and a solvent.

The following Base/solvent combinations are used:

| Example | Base | Solvent |
| --- | --- | --- |
| Example A22.1 | DBU (1,8-diazabicyclo[5.4.0]undec-7-ene | dimethylformamide |
| Example A22.2 | DBN (1,5-diazabicyclo[4.3.0]non-5-ene) | dimethylacetamide |
| Example A22.3 | DBN (1,5-diazabicyclo[4.3.0]non-5-ene) | 1-methylpyrrolidone |
| Example A22.4 | DBN (1,5-diazabicyclo[4.3.0]non-5-ene) | dimethylsulfoxide |
| Example A22.5 | DBU (1,8-diazabicyclo[5.4.0]undec-7-ene | dimethylformamide |
| Example A22.6 | dibutylamine | dimethylacetamide |
| Example A22.7 | N-methylmorpholine | 1-methylpyrrolidone |
| Example A22.8 | sodium methylate | dimethylsulfoxide |

82.49 grams of the crude product (24) are obtained yielding a black oil.

Example A23

Preparation of the Compound (11)

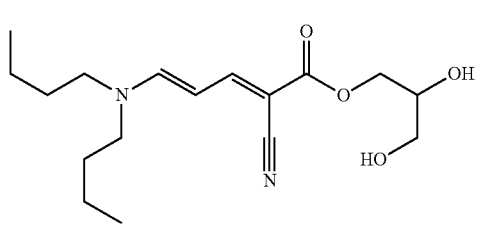
(11)

80 ml of hydro chloride acid (1 N) are added to a solution of 82.5 grams of crude merocyanine (24) in 250 ml of ethanol. The reaction mixture is stirred for 16 hours at room temperature. After removal of ethanol in vacuum the reaction mass is taken up in water and the product is extracted several times with ethyl acetate.

The collected organic phases are concentrated in vacuum.

After silica gel column chromatography (eluent: toluene/acetone) 37.85 grams of the desired product are obtained yielding a brownish oil.

HPLC (210 nm): 99.3 A-%. 1H-NMR (CDCl3): δ=7.8 (1H, d), 7.2 (1H, d), 5.6 (1H, t), 4.27 (2H, m), 3.98 (1H, m), 3.5-3.7 (2H, m), 3.25-3.33 (4H, m), 3.00 (2H, s), 1.61 (4H, m), 1.35 (4H, m), 0.96 (6H, m).

Example A24

Preparation of the Compound (25)

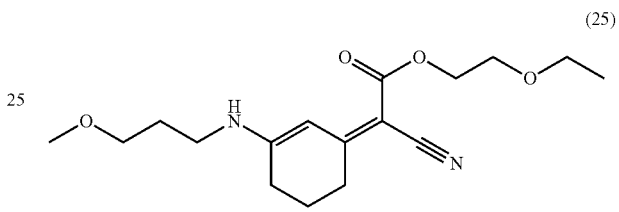
(25)

148.4 grams of 3-[(3-methoxypropyl)amino]-2-cyclohexen-1-one are alkylated with dimethylsulfate or alternatively with diethylsulfate and treated with 130.00 grams of 2-ethoxyethyl cyanoacetate in the presence of an organic base and a solvent.

The following base/solvent combinations are used:

| Example | Base | Solvent |
| --- | --- | --- |
| Example A24.1 | DBU (1,8-diazabicyclo[5.4.0]undec-7-ene) | dimethylacetamide |
| Example A24.2 | triethylamine | isopropanol |
| Example A24.3 | 3-methoxypropylamine | isopropanol |
| Example A24.4 | N-methylmorpholine | tert-amylalcohol |
| Example A24.5 | 3-methoxypropylamine | toluene |
| Example A24.6 | 3-methoxypropylamine | dimethylformamide |
| Example A24.7 | 3-methoxypropylamine | no solvent |

UV Shielding Properties

The UV shielding properties of the merocyanine derivatives are investigated by measuring their UV spectra in ethanol. In the following table the investigated absorption maxima (Amax) together with the corresponding $A^{1\%}_{1cm}$ values are listed.

| | Absorption maximum | |
| --- | --- | --- |
| Comp. No. | λmax | $A^{1\%}_{1\,cm}$ |
| (1) | 380 | 2283 |
| (2) | 380 | 2046 |

| Comp. No. | Absorption maximum | |
|---|---|---|
| | λmax | $A^{1\%}_{1\,cm}$ |
| (3) | 380 | 1965 |
| (4) | 381 | 2568 |
| (5) | 381 | 2252 |
| (6) | 380 | 2530 |
| (7) | 381 | 2467 |
| (9) | 380 | 2414 |
| (12) | 381 | 2235 |
| (14) | 385 | 2207 |
| (15) | 385 | 1644 |
| (16) | 386 | 1618 |
| (17) | 385 | 2083 |
| (18) | 385 | 2036 |
| (23) | 381 | 2230 |
| (25) | 385 | 1947 |

All merocyanine compounds according to the present invention possess extraordinary high shielding properties in the UV region as indicated by $A^{1\%}_{1\,cm}$ cm values above 1500.

B. Examples of Cosmetic Formulations

Examples 1-3

O/W Emulsions

| Ingredients | 1 | 2 | 3 |
|---|---|---|---|
| Caprylyl glycol | 0.5 | 0.5 | 0.5 |
| Caprylic/Capric Triglyceride and Sodium Acrylates Copolymer (Luvigel EM-BASF) | 3 | 3 | 3 |
| Triethanolamine | 0.2 | 0.2 | 0.2 |
| Ethylhexyl salicylate | 5 | 5 | 5 |
| Drometrizole trisiloxane | 2 | 2 | 2 |
| Inulin Lauryl Carbamate (Inutec SP1-ORAFTI) | 0.3 | 0.3 | 0.3 |
| Cyclohexasiloxane | 2 | 2 | 2 |
| Glycerin | 5 | 5 | 5 |
| Propylene glycol | 10 | 10 | 10 |
| $C_{12}$-$C_{15}$-Alkyl Benzoate (Finsolv TN-INNOSPEC ACTIVE CHEMICAL) | 7 | 7 | 7 |
| Octocrylene | 7 | 7 | 7 |
| Butyl methoxydibenzoylmethane | 3 | 3 | 3 |
| Merocyanine compound (4) | 2 | | |
| Merocyanine compound (15) | — | 2 | — |
| Merocyanine compound (14) | — | — | 3 |
| Terephthalylidene Dicamphor Sulfonic acid | 0.5 | 0.5 | 0.5 |
| Preservative | 0.8 | 0.8 | 0.8 |
| Disodium EDTA | 0.1 | 0.1 | 0.1 |
| Water | qs 100 | qs 100 | qs 100 |

Examples 4-5

W/O Emulsions

| Ingredients | 4 | 5 |
|---|---|---|
| Isopropyl lauroyl sarcosinate (Eldew SL-205-Ajinomoto U.S.A., Inc.) | 3 | 3 |
| Triethanolamine | 0.9 | 0.9 |
| Drometrizole trisiloxane | 7 | 7 |
| Synthetic wax (Cirebelle 303-SASOL) | 2 | 2 |
| Cyclohexasiloxane | 7 | 7 |
| Glycerine | 5 | 5 |
| Dimethicone | 8 | 8 |
| $C_{12}$-$C_{15}$-Alkyl Benzoate (Finsolv TN-INNOSPEC ACTIVE CHEMICAL) | 5 | 5 |
| Octocrylene | 7 | 7 |
| Butyl methoxydibenzoylmethane | 3 | 3 |
| Terephthalylidene Dicamphor Sulfonic Acid | 0.5 | 0.5 |
| Preservatives | 0.8 | 0.8 |
| Disodium EDTA | 0.2 | 0.2 |
| Merocyanine compound (25) | 3 | — |
| Merocyanine compound (27) | | 3 |
| Dimethicone/PEG-10/15 crosspolymer (KSG-210-Shin-Etsu Chemical Co.) | 4.2 | 4.2 |
| Dimethicone crosspolymer (Dow Corning 9041 Silicone Elastomer Blend-Dow Corning Corporation) | 0.2 | 0.2 |
| Hydrogenated Polyisobutene | 5 | 5 |
| Aluminium Starch Octenyl succinate (Dry-Flo Pure-AkzoNobel Global Personal Care) | 2 | 2 |
| Water | qs 100 | qs 100 |

Examples 6-8

W/O Emulsions

| Phase | Ingredients | 6 | 7 | 8 |
|---|---|---|---|---|
| A | Glycerol | 5 | 5 | 5 |
| | EDTA | 0.1 | 0.1 | 0.1 |
| | POTASSIUM CETYL PHOSPHATE | 1 | 1 | 1 |
| | Deionized Water | qsp 100 | qsp 100 | qsp 100 |
| | Triethanolamine | 0.3 | 0.3 | 0.3 |
| | Preservatives | 1.2 | 1.2 | 1.2 |
| B1 | PHENETHYL BENZOATE (and) BENZOIC ACID | 30 | 30 | 30 |
| | Preservatives | 0.25 | 0.25 | 0.25 |
| | STEARIC ACID | 1.5 | 1.5 | 1.5 |
| | GLYCERYL STEARATE (and) PEG-100 STEARATE | 1 | 1 | 1 |
| | Cetyl alcohol | 0.5 | 0.5 | 0.5 |
| | Cetearyl alcohol and cetearyl glucoside | 2 | 2 | 2 |
| | POLY DIMETHYLSILOXANE (VISCOSITY: 350 CST) | 0.5 | 0.5 | 0.5 |
| | TRIETHANOLAMINE | 0.45 | 0.45 | 0.45 |
| | Merocyanine compound 4 | 2 | 0 | 0 |
| | Merocyanine compound 14 | 0 | 2 | 0 |
| | Merocyanine compound 15 | 0 | 0 | 2 |
| B2 | Isohexadecane | 1 | 1 | 1 |
| | ACRYLATES/C10-30 ALKYL ACRYLATE CROSSPOLYMER | 0.2 | 0.2 | 0.2 |
| | Xanthan gum | 0.2 | 0.2 | 0.2 |
| | Cyclopentadimethylsiloxane | 5 | 5 | 5 |

The UV protection efficacy of these compositions has been evaluated.

Emulsification Protocol:

Aqueous and oil Phases A and B are prepared by mixing the raw materials under stirring at 80° C.; the obtained solutions are macroscopically homogeneous. Emulsions are prepared by slow introduction of the oil phase B1 in the aqueous phase under shearing using a rotor/stator Moritz homogenizer at the rotating speed of 4000 RPM during 15 minutes. The emulsion temperature is then decreased from 80° C. down to 40° C. under stirring. Oil phase B2 is then introduced in the emulsion under low shear. The emulsion is cooled down to room temperature under low shear. The emulsion is characterized by droplets which size is between 1 µm and 10 µm.

In vitro Evaluation protocol of UV protection efficacy The Persistant Pigmentation Darkening (PPD) is determined using the in vitro method described by B. L. Diffey in the paper J. Soc. Cosmet. Chem. 40, 127-133, (1989) for Sun Protection Factor (SPF). Measurements are carried out using a Labsphere UV-1000S spectrophotometer. Formulae are applied on a rough PPMA plate, to get a homogeneous film at the rate of 1 mg/cm².

Results

TABLE I

| | Examples | | |
|---|---|---|---|
| | Example 6 | Example 7 | Example 8 |
| PPD in vitro | 6.3 +/− 0.3 | 4.6 +/− 0.2 | 5.2 +/− 0.5 |

Examples 9

W/O Emulsions

| Phase | Ingrédients | 9 |
|---|---|---|
| A | Glycerine | 5 |
| | EDTA | 0.1 |
| | POTASSIUM CETYL PHOSPHATE | 1 |
| | Deionized Water | qsp 100 |
| | Triethanolamine | 0.3 |
| | Preservatives | 1.2 |
| B1 | PHENETHYL BENZOATE (and) BENZOIC ACID | 30 |
| | Preservatives | 0.25 |
| | STEARIC ACID | 1.5 |
| | GLYCERYL STEARATE (and) PEG-100 STEARATE | 1 |
| | Cetyl alcohol | 0.5 |
| | Cetearyl alcohol and cetearyl glucoside | 2 |
| | POLY DIMETHYLSILOXANE (VISCOSITY: 350 CST) | 0.5 |
| | TRIETHANOLAMINE | 0.45 |
| | 4-ter-butyl-4′-methoxydibenzoyl méthane | 2 |
| | Merocyanine compound 4 | 1 |
| B2 | Isohexadecane | 1 |
| | ACRYLATES/C10-30 ALKYL ACRYLATE CROSSPOLYMER | 0.2 |
| | Xanthan gum | 0.2 |
| | Cyclopentadimethylsiloxane | 5 |

Protocol of Evaluation of the Photostabilty of the UV Filters

The percentage of residual amount of each UV filter (merocyanine compound and dibenzoylmethane compound) caused by the exposure to a solar simulator of a formula spread in a film having a thickness of about 20 µm was measure.

The evaluation was done by HPLC analysis of each UV filter in a solution after extraction of the film, by comparing exposed and non-exposed samples.

Material and Method:

Solar simulator: Apparatus Oriel 1000W equipped with a 4 pouces outlet, a 81017 filter and a dichroic mirror. The samples were exposed in horizontal position.

UV-Meter: Apparatus OSRAM CENTRA equipped with two reading heads, one for the UVA radiation and the other one for the UVB radiation.

The simulator and UV meter are together calibred annually by spectroradiometry.

Exposure measurements were done at the beginning and at the end of the exposure by positioning the reading heads at the position of the sample.

The UV exposure was characterized by:
a UVB flux of 0.35-0.45 mW/cm²
a UVA flux 16-18 mW/cm².

Each residual amount of each UV filter was measured by HPLC chromatography with a sensor having diodes bars.

Each residual amount of each UV filter was measured by HPLC chromatography with a sensor having diodes bars.

Photostability Tests

About 20 mg of the composition are spread on the surface of a rough melt silica disc.

3 films of composition were exposed to the solar simulator and 3 other films were used as control.

The samples were exposed 3 per 3 to the light of the simulator during a sufficient time delivering an UVA dose of 42 J/cm².

At the end of the exposure, the disc was introduced in a bowl of 600 ml with 10 ml of appropriate solvent (ie generally ethanol). The disc and the bowl were then placed during 5 minutes in an ultrasonic tank.

The solutions were then transferred in appropriate bottles compatibles with the HPLC chromatograph.

Results

TABLE II

| Measurements of Photostability | Example 9 |
|---|---|
| % of residual merocyanine compound 4 after UV exposure | 85 |
| % of residual Avobenzone after UV exposure | 91 |

It was observed that, in the composition 9, the photostability of the merocyanine compound of the invention and the photostability of the dibenzoylmethane are both satisfactory.

Stability Tests for Compounds 15 and 25

The chemical stability of the compounds can be assessed in a water/ethanol solution 1/1 with compounds solubilized at 0.5%.

These solutions could be acidified to check also stability toward acid media for example HCl 0.1M in a water/ethanol/isopropanol 50/40/10 (v/v/v).

Once the solution prepared, it is placed in an oven at 45° C. for 2 months for stability and 1 h at 60° C. for acidic stress. Then the solution is aliquoted (0.005% w/v in H2O/ACN 50/50) for liquid chromatography analysis to check disappearance or not.

Materials and Methods:

UPLC Acquity (Waters) with diod array detector eλ (Waters).

Column: Acquity HSS T3 (Waters), length: 50 mm, Inner diameter: 2.1 mm, particles diameter 1.8 µm. Mobile phase A=ammonium acetate 20 mM, B=Acetonitrile.

| Linear gradient t (minutes) | % A | % B |
|---|---|---|
| 0 | 95 | 05 |
| 5 | 05 | 95 |
| 8 | 05 | 95 |
| 8.5 | 95 | 05 |
| 10 | 95 | 05 |

Flow rate: 0.5 mL/min
T: 20° C.
Detection at UV 383 nm
Analysis: 1 µL injection
Elution time of compound 25: 2.56 min
Elution time of compound 15: 2.11 min
Acid media stability

| Compounds | Storage stability 2 months 45° C. | Acid media stability 1 h 60° C. |
|---|---|---|
| 15 | No loss | Loss 100% |
| 25 | No loss | Loss 4% |

These results show the superiority of compound 25 versus 15.

The invention claimed is:

1. A cosmetic and/or dermatological composition comprising in a physiologically acceptable medium in an amount of from 0.1% to 10% by weight based upon the weight of the composition of at least one merocyanine derivative of formula (1) or (2) and/or its E/E-, E/Z- or Z/Z geometrical isomer forms:

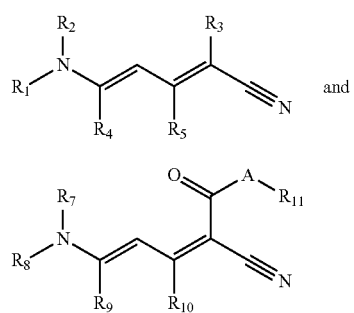

wherein
$R_1$ and $R_2$ independently of each other are hydrogen; $C_4$-$C_{12}$alkyl; or hydroxyl-$C_3$-$C_{12}$alkyl;
$R_3$ is a —(C═O)OR6group; or a —(CO)NHR$_6$group;
$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which optionally contains in its chain one or more than one —O— or by —NH—;
n is a number from 2 to 7;

$R_7$ and $R_8$ independently of each other are hydrogen; $C_1$-$C_{22}$alkyl, $C_2$-$C_{22}$alkenyl, $C_2$-$C_{22}$alkinyl, which optionally contains in its chain one or more than one O and/or substituted by one or more than one OH, $C_3$-$C_{22}$cycloalkyl or $C_3$-$C_{22}$cycloalkenyl, wherein said $C_3$-$C_{22}$cycloalkyl or $C_3$-$C_{22}$cycloalkenyl optionally contains in its chain one or more than one —O—;
or $R_7$ and $R_8$ together with the nitrogen atom linking them form a —(CH$_2$)$_n$— ring which optionally contains in its chain one or more than one —O—;
$R_9$ and $R_{10}$ are hydrogen; or $R_9$ and $R_{10}$ form a —(CH$_2$)$_n$— ring which is optionally substituted by C1-C4alkyl and/or contains in its chain —O— or —NH—;
A is —O—; or —NH;
$R_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which optionally contains in its chain one or more than one O; or $C_1$-$C_{22}$alkyl or $C_2$-$C_{22}$alkenyl which is substituted by $C_3$-$C_{22}$cycloalkyl or $C_3$-$C_{22}$cycloalkenyl, wherein said $C_3$-$C_{22}$cycloalkyl or $C_3$-$C_{22}$cycloalkenyl optionally contains in its chain one or more than one —O—;
with the proviso that
(I) at least one of $R_1$, $R_2$ and $R_6$ is substituted by hydroxy; with the proviso that when both $R_1$ and $R_2$ are hydrogen, $R_6$ is substituted by hydroxyl;
(II) if R1 is hydrogen, $R_2$ is not 1-hydroxy-3-methyl-but-2-yl;
(III) if $R_6$ is substituted by one or more than one OH; one of $R_1$ and $R_2$ is $C_4$-$C_{22}$alkyl; or $R_1$ and $R_2$ together with the linking nitrogen form a piperidyl or morpholinyl radical;
(IV) at least one of $R_7$ and $R_8$, or $R_{11}$ contains in its chain one or more than one —O—; and
at least one active agent in a content ranging from 0.001% to 20% by weight relative to the total weight of the composition selected from the group of moisturizers, desquamating agents, agents for improving the barrier function, depigmenting agents, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, lipid restructuring agents, agents promoting the cutaneous microcirculation for the area around the eyes and agents which promote the natural colouring of the skin.

2. The cosmetic and/or dermatological composition according to claim 1,
$R_1$ and $R_2$ independently of each other are hydrogen; $C_4$-$C_{12}$alkyl; or hydroxyl-$C_3$-$C_{12}$alkyl;
$R_3$ is a —(C═O)OR$_6$group; or a —(CO)NHR$_6$group;
$R_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R_4$ and $R_5$ are hydrogen; or $R_4$ and $R_5$ form a —(CH$_2$)$_n$— ring which optionally contains in its chain —O— or by —NH—;
n is a number from 2 to 7;
$R_7$ and $R_8$ independently of each other are hydrogen; $C_1$-$C_{22}$alkyl, $C_2$-$C_{22}$alkenyl, $C_2$-$C_{22}$alkinyl, which is optionally interrupted by one or more than one O and/or substituted by one or more than one OH; or $R_7$ and R$_8$ together with the nitrogen atom linking them form a —(CH$_2$)$_n$— ring which is optionally interrupted by one or more than one —O—;

R$_9$ and R$_{10}$ are hydrogen; or R$_9$ and R$_{10}$ form a —(CH$_2$)$_n$— ring which is optionally substituted by C$_1$-C$_4$alkyl and/or interrupted by —O— or by —NH—;

A is —O—; or —NH;

R$_{11}$ is C$_1$-C$_{22}$alkyl, C$_2$-C$_{22}$alkenyl, C$_2$-C$_{22}$alkinyl, C$_3$-C$_{22}$cycloalkyl or C3-C22cycloalkenyl, which is optionally interrupted by one or more than one O;

with the proviso that (I) at least one of R$_1$, R$_2$ and R$_6$ is substituted by hydroxy;

(II) if one of R$_1$ is hydroxyethyl, R$_2$ is not hydrogen, methyl or ethyl or hydroxyethyl; and if R$_1$ is hydrogen, R$_2$ is not 1-hydroxy-3-methyl-but-2-yl;

(III) if R$_6$ is substituted by one or more than one OH; one of R$_1$ and R$_2$ is C$_4$-C$_{22}$alkyl; or R$_1$ and R$_2$ together with the linking nitrogen form a piperidyl or morpholinyl radical;

(IV) at least one of R$_7$ and R$_8$, or R$_{11}$ is interrupted by one or more than one —O—;

of the at least one merocyanine derivative.

3. The cosmetic and/or dermatological composition of formula (1) according to claim 1, wherein R$_6$ is C$_1$-C$_{12}$alkyl, which is optionally substituted by one or more than one hydroxyl; of the at least one merocyanine derivative.

4. The cosmetic and/or dermatological composition of formula (1) according to claim 1, wherein R$_6$ is C$_1$-C$_{12}$alkyl which is substituted by one or more than one hydroxy;
one of R$_1$ and R$_2$ is C$_4$-C$_{22}$alkyl; or R$_1$ and R$_2$ together with the nitrogen atom linking them form a —(CH$_2$) n-ring which is optionally interrupted by —O— and/or —NH; of the at least one merocyanine derivative.

5. The cosmetic and/or dermatological composition according to claim 1, in which the compounds of formula (1) in said composition are selected from those wherein
R$_3$ is a —(C═O)OR$_6$group; or a —(C═O)NHR$_6$group;
R$_6$ is C$_1$-C$_{22}$alkyl; and
R$_4$ and R$_5$ are hydrogen; or R$_4$ and R$_5$ are linked together to form a carbocyclic ring which contains 6 carbon atoms.

6. The cosmetic and/or dermatological composition according to claim 1, in which the compounds of formula (2) in said composition are selected from those wherein R$_7$ and R$_8$ independently of each other are hydrogen or C$_1$-C$_8$alkyl, which optionally contains in its chain one or more than one —O—;
A is —O—; or —NH;
R$_{11}$ is C$_1$-C$_{22}$alkyl; and
R$_9$ and R$_{10}$ are hydrogen; or R$_9$ and R$_{10}$ are linked together to form a carbocyclic ring which contains 6 carbon atoms.

7. The cosmetic and/or dermatological composition according to claim 1, in which the compounds of formula (2) in said composition are selected from those wherein R$_7$ and R$_8$ together with the nitrogen atom form a morpholinyl or piperidyl radical;
A is —O—; or —NH;
R$_{11}$ is C$_1$-C$_{22}$alkyl; which is interrupted by one or more than one —O—; and
R$_9$ and R$_{10}$ are hydrogen; or R$_9$ and R$_{10}$ are linked together to form a carbocyclic ring which contains 6 carbon atoms.

8. The cosmetic and/or dermatological composition according to claim 7, in which the compounds of formula (2) in said composition are selected from those, wherein R$_{11}$ is a radical of —(CH$_2$)$_m$—O—R$_{12}$, wherein
R$_{12}$ is C$_1$-C$_4$alkyl; or C$_1$-C$_4$alkoxy-C$_1$-C$_4$alkyl;
m is a number from 1 to 3;
R$_7$ and R$_8$, independently of each other are hydrogen;
C$_1$-C$_{12}$alkyl, which is optionally interrupted by one or more than one O; or R$_7$ and R$_8$ together with the nitrogen atom form a morpholinyl or piperidyl radical;
R$_9$ and R$_{10}$ are hydrogen; or form a carbocyclic ring which contains 6 carbon atoms; and
A is —O—; or —NH.

9. The cosmetic and/or dermatological composition according to claim 1, further containing a system for screening out both UVA radiation and UVB radiation.

10. The cosmetic and/or dermatological composition according to claim 1, further containing one or more complementary hydrophilic, lipophilic or insoluble organic screening agents and/or one or more inorganic screening agents which are active in UVA and/or UVB.

11. The cosmetic and/or dermatological composition according to claim 1, further containing at least one dibenzoylmethane derivative.

12. The cosmetic and/or dermatological composition according to claim 1, containing at least one dibenzoylmethane derivative and the merocyanine compound the compound 2-ethoxyethyl (2Z)-cyano{3-[(3-methoxypropyl)amino]cyclohex-2-en-1-ylidene}ethanoate (25) in its E/Z geometrical isomer form of formula:

and/or its E/E geometrical isomer form of formula:

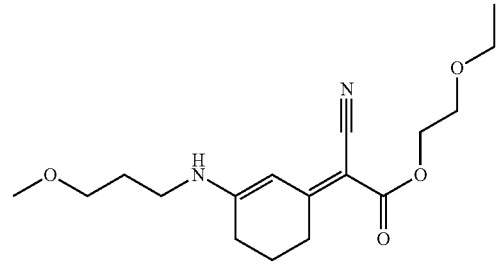

13. The cosmetic and/or dermatological composition according to claim 1, containing at least one fatty substance selected from oils and waxes.

14. The cosmetic and/or dermatological composition according to claim 1, containing at least one hydrophilic or lipophilic thickener.

15. The cosmetic and/or dermatological composition according to claim 1, containing at least one emulsifier of the type hydrophobically modified inuline as Inuline Lauryl Carbamate.

16. The cosmetic and/or dermatological composition according to claim 1, containing at least one depigmenting agent.

17. A cosmetic and/or dermatological process for protecting the keratinic materials which comprises the application onto the keratinic material of a cosmetic composition as defined in claim 1.

18. The cosmetic and/or dermatological composition according to claim 1, wherein the at least one depigmenting agent is at least one hydroxylated diphenylmethane derivative.

19. The cosmetic and/or dermatological composition according to claim 1, which comprises at least one active agent selected from the group of moisturizers, desquamating agents, agents for improving the barrier function, depigmenting agents, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, NO-synthase inhibitors, and agents for stimulating the energy metabolism of cells.

20. A cosmetic and/or dermatological process for controlling and/or improving the darkening of the skin under exposure to UV radiation and the homogeneity of the colour of the complexion which comprises the application onto the skin of a cosmetic composition as defined in claim 1.

21. The cosmetic and/or dermatological process according to claim 20, wherein the hydroxylated diphenylmethane derivative has the structure:

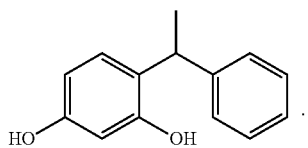

22. A cosmetic and/or dermatological composition comprising in a physiologically acceptable medium in an amount of from 0.1% to 10% by weight based upon the weight of the composition of at least one merocyanine derivative selected from the group of the following compounds and their E/E, E,Z or Z/Z geometrical isomer forms:

4

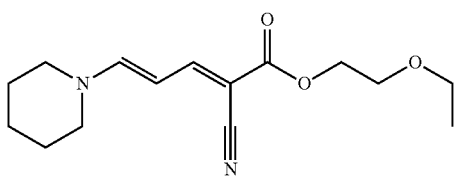

2-ethoxyethyl (2E,4E)-2-cyano-5-(piperidin-1-yl)penta-2,4-dienoate

14

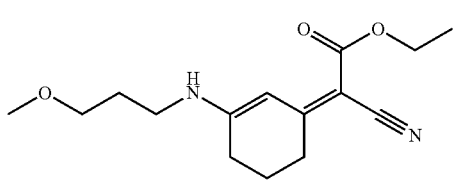

ethyl (2Z)-cyano{3-[(3-methoxypropyl)amino]cyclohex-2-en-1-ylidene}ethanoate

-continued

15

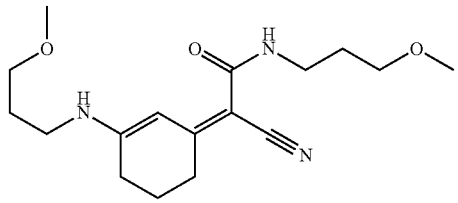

(2Z)-2-cyano-N-(3-methoxypropyl)-2-{3-[(3-methoxypropyl)amino]cyclohex-2-en-1-ylidene}ethanamide

25

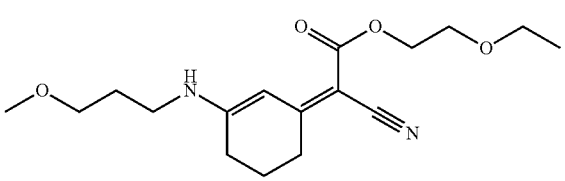 [SMILES: CCOCCOC(=O)/C(C#N)=C1\C=C(NCCCOC)CCC1]

2-ethoxyethyl (2Z)-cyano{3-[(3-methoxypropyl)amino]cyclohex-2-en-1-ylidene}ethanoate

27

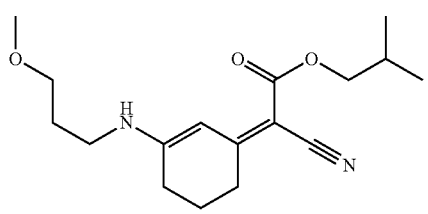

2-methylpropyl (2Z)-cyano{3-[(3-methoxypropyl)amino]cyclohex-2-en-1-ylidene}ethanoate

29

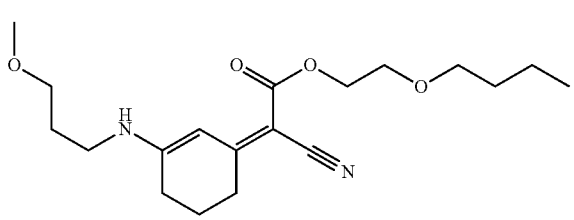

31

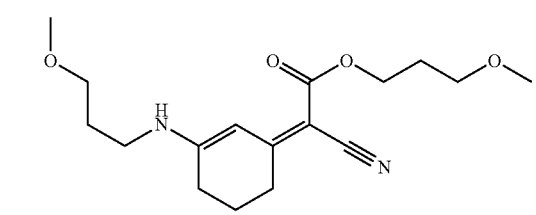

37

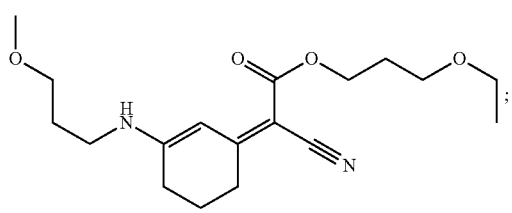

and at least one active agent in a content ranging from 0.001% to 20% by weight relative to the total weight of the composition selected from the group of moisturizers, desquamating agents, agents for improving the barrier function, depigmenting agents, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, lipid restructuring agents, agents promoting the cutaneous microcirculation for the area around the eyes and agents which promote the natural colouring of the skin.

23. The cosmetic and/or dermatological composition according to claim 22, wherein the merocyanine derivative in said composition is the compound 2-ethoxyethyl (2Z)-cyano{3-[(3-methoxypropyl)amino]cyclohex-2-en-1-ylidene}ethanoate (25) in its E/Z geometrical isomer form of formula:

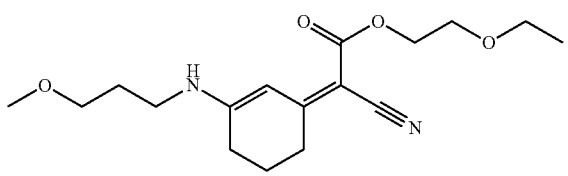 [SMILES: CCOCCOC(=O)/C(C#N)=C1\C=C(NCCCOC)CCC1]

and/or its E/E geometrical isomer form of formula:

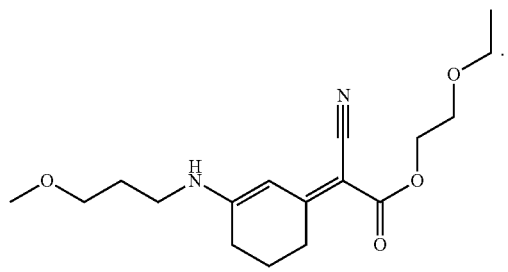 [SMILES: CCOCCOC(=O)/C(C#N)=C1/C=C(NCCCOC)CCC1]

24. The cosmetic and/or dermatological composition according to claim 22, further containing at least one dibenzoylmethane derivative; at least one fatty substance selected from oils and waxes; at least one hydrophilic or lipophilic thickener; at least one emulsifier of the type hydrophobically modified inuline; and at least one hydroxylated diphenylmethane derivative.

25. A cosmetic and/or dermatological composition for improving the skin against photo-aging, comprising in a physiologically acceptable medium at least one merocyanine derivative of formula (3) and/or the E/E-, E/Z- or Z/Z geometrical isomer forms thereof:

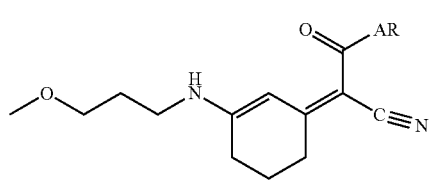

(3)

wherein:
A is —O— or —NH;
R is a $C_2$-$C_6$ alkyl group, which is optionally interrupted with one or more O.

26. A method for protecting a body care product from photolytic and oxidative degradation, which comprises incorporating in the body care product at least one merocyanine derivative of formula (1') or (2') and/or its E/E-, E/Z- or Z/Z geometrical isomer forms:

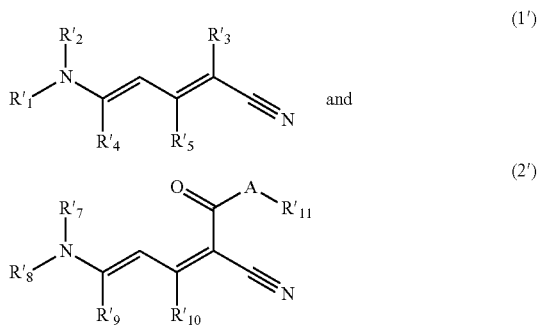

$R'_1$ and $R'_2$ independently of each other are hydrogen; $C_4$-$C_{12}$alkyl; or hydroxyl-$C_3$-$C_{12}$alkyl;
$R'_3$ is a —(C=O)OR$_6$group; or a —(CO)NHR'$_6$group;
$R'_6$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which is optionally substituted by one or more than one OH;
$R'_4$ and $R'_5$ are hydrogen; or $R'_4$ and $R'_5$ form a —(CH$_2$)$_n$— ring which is optionally contains in its chain —O— or by —NH—;
n is a number from 2 to 7;
$R'_7$ and $R'_8$ independently of each other are hydrogen; $C_1$-$C_{22}$alkyl, $C_2$-$C_{22}$alkenyl, $C_2$-$C_{22}$alkinyl, which is optionally contains in its chain one or more than one O; or $R'_7$ and $R'_8$ together with the nitrogen atom linking them form a —(CH$_2$)$_n$— ring which optionally contains in its chain one or more than one —O—;
$R'_9$ and $R'_{10}$ are hydrogen; or $R'_9$ and $R'_{10}$ form a —(CH$_2$)$_n$— ring which is optionally substituted by $C_1$-$C_4$alkyl and/or optionally contains in its chain —O— or —NH—;
A is —O—; or —NH;
$R'_{11}$ is $C_1$-$C_{22}$alkyl, $C_2$-$C_{22}$alkenyl, $C_2$-$C_{22}$alkinyl, $C_3$-$C_{22}$cycloalkyl or $C_3$-$C_{22}$cycloalkenyl, which optionally contains in its chain one or more than one O;
with the proviso that
(I) at least one of $R'_1$, $R'_2$ and $R'_6$ is substituted by hydroxy; with the proviso that when both $R'_1$ and $R'_2$ are hydrogen, $R'_6$ is substituted by hydroxyl;
(II) if R'1 is hydrogen, $R'_2$ is not 1-hydroxy-3-methyl-but-2-yl;
(III) if $R'_6$ is substituted by one or more than one OH; one of $R'_1$ and $R'_2$ is $C_4$-$C_{22}$alkyl; or
$R'_1$ and $R'_2$ together with the linking nitrogen form a piperidyl or morpholinyl radical;
(IV) at least one of $R'_7$ and $R'_8$, or $R'_{11}$ contains in its chain one or more than one —O—;
wherein the product comprises a physiologically acceptable medium and at least one active agent in a content ranging from 0.001% to 20% by weight relative to the total weight of the composition selected from the group of moisturizers, desquamating agents, agents for improving the barrier function, depigmenting agents, dermo-decontracting agents, anti-glycation agents, agents for stimulating the synthesis of dermal and/or epidermal macromolecules and/or for preventing their degradation, agents for stimulating fibroblast or keratinocyte proliferation and/or keratinocyte differentiation, agents for promoting the maturation of the horny envelope, NO-synthase inhibitors, peripheral benzodiazepine receptor (PBR) antagonists, agents for increasing the activity of the sebaceous glands, agents for stimulating the energy metabolism of cells, lipid restructuring agents, agents promoting the cutaneous microcirculation for the area around the eyes and agents which promote the natural colouring of the skin; and wherein the amount of the at least one merocyanine derivative is from 0.1% to 10% by weight based upon the weight of the composition.

\* \* \* \* \*